United States Patent
Fotsch et al.

(10) Patent No.: US 11,581,076 B2
(45) Date of Patent: *Feb. 14, 2023

(54) METHODS AND APPARATUSES FOR PROVIDING ALTERNATIVES FOR PREEXISTING PRESCRIBED MEDICATIONS

(71) Applicant: Gemini Health LLC, Sausalito, CA (US)

(72) Inventors: Edward Fotsch, Sausalito, CA (US); Roger Pinsonneault, Johns Creek, GA (US)

(73) Assignee: Gemini Health LLC, Sausalito, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/402,406

(22) Filed: Aug. 13, 2021

(65) Prior Publication Data
US 2021/0375413 A1  Dec. 2, 2021

Related U.S. Application Data

(63) Continuation of application No. 16/036,851, filed on Jul. 16, 2018, now Pat. No. 11,127,490.

(60) Provisional application No. 62/670,146, filed on May 11, 2018, provisional application No. 62/667,141, filed on May 4, 2018, provisional application No. 62/645,350, filed on Mar. 20, 2018, provisional application No. 62/618,296, filed on Jan. 17, 2018.

(51) Int. Cl.
*G16H 10/60* (2018.01)
*G16H 20/10* (2018.01)

(52) U.S. Cl.
CPC ........... *G16H 10/60* (2018.01); *G16H 20/10* (2018.01)

(58) Field of Classification Search
CPC ......... G16H 10/60; G16H 20/10; G16H 40/20
See application file for complete search history.

(56) References Cited

U.S. PATENT DOCUMENTS

| 7,769,601 | B1 | 8/2010 | Bleser et al. |
| 11,127,490 | B2 | 9/2021 | Fotsch et al. |
| 2003/0050799 | A1 | 3/2003 | Jay et al. |
| 2007/0067186 | A1* | 3/2007 | Brenner ............... G16H 20/10 705/2 |

(Continued)

FOREIGN PATENT DOCUMENTS

| WO | WO2014/151911 A1 | 9/2014 | |
| WO | WO-2014151911 A1 * | 9/2014 | ............. G16H 10/60 |

OTHER PUBLICATIONS

Johansen ME, Richardson C. Estimation of Potential Savings Through Therapeutic Substitution, JAMA Intern Med. 2016;176(6): 769-775. doi:10.1001/jamainternmed.2016.1704 (Year: 2016).*

(Continued)

*Primary Examiner* — Rachelle L Reichert
(74) *Attorney, Agent, or Firm* — Shay Glenn LLP

(57) ABSTRACT

Methods and apparatuses for automatically identifying therapeutically equivalent alternative medications for reducing patient costs. These methods and apparatuses may interface with a patient's electronic health records and Payer databases and identify alternative medications that offer cost savings to the patient and Payer. The methods and apparatuses described herein may also incentivize patients to select cost-saving medication alternatives.

20 Claims, 12 Drawing Sheets

(56) References Cited

U.S. PATENT DOCUMENTS

| | | | |
|---|---|---|---|
| 2007/0162303 A1* | 7/2007 | Wiley, II | G16H 20/10 |
| | | | 705/400 |
| 2007/0226009 A1* | 9/2007 | Hicks | G06Q 40/08 |
| | | | 600/300 |
| 2007/0250341 A1 | 10/2007 | Howe et al. | |
| 2010/0057489 A1 | 3/2010 | Howe et al. | |
| 2010/0161353 A1 | 6/2010 | Mayaud | |
| 2011/0184753 A1* | 7/2011 | Tripoli | G06Q 10/06 |
| | | | 715/769 |
| 2014/0244279 A1* | 8/2014 | Bezdek | G06Q 30/0613 |
| | | | 705/2 |
| 2014/0278495 A1 | 9/2014 | Rourke et al. | |
| 2014/0278520 A1 | 9/2014 | Abuzeni et al. | |
| 2015/0178808 A1 | 6/2015 | Grossman et al. | |
| 2016/0188820 A1 | 6/2016 | Brown et al. | |
| 2018/0075212 A1* | 3/2018 | Kubey | G06Q 10/087 |
| 2021/0313032 A1 | 10/2021 | Fotsch et al. | |

OTHER PUBLICATIONS

Fotsch; U.S. Appl. No. 15/428,084 entitled "Systems and methods for prescription pricing transparency," filed Feb. 8, 2017.
Johansen et al.; Estimation of potential savings through therapeutic substitution; JAMA Internal Medicine; 176(6); pp. 769-775; Jun. 2016.

* cited by examiner

Drug Savings Report

Member: Patricia Brown  Total Savings[1] > $35,000

| Current Medication | Alternative Medication | Annual Total Savings[2] | Annual Patient Savings[3] |
|---|---|---|---|
| Edarbyclor 40mg-25mg Tablet Source: PBM Dr. Robert Smith (415) 555-1212 | Irbesartan/HCTZ 150-12.5mg Tablet Qty: 30 | $1,996 | $1,012 |
| | Valsartan/HCTZ 80mg-12.5mg Tablet Qty: 30 | $2,089 | $1,105 |
| Zyflo CR 600mg ER Tablet Source: PBM Dr. Robert Smith (415) 555-1212 | Montelukast 10mg Tablet Qty: 30 | $11,045 | $2,953 |
| | Zafirlukast 20mg Tablet Qty: 60 | $9,958 | $1,865 |
| | Zafirlukast 10mg Tablet Qty: 120 | $8,836 | $1,807 |
| Coreg CR 20mg ER Capsule Source: PBM Dr. Robert Smith (415) 555-1212 | Carvedilol 25mg Tablet Qty: 30 | | |
| | Carvedilol 12.5mg Tablet Qty: 60 | | |
| | Carvedilol 6.25mg Tablet Qty: 90 | | |
| Glumetza 500mg ER Tablet Source: PBM Dr. Robert Smith (415) 555-1212 | Metformin 500mg Tablet Qty: | | |
| | Metformin 500mg ER | | |

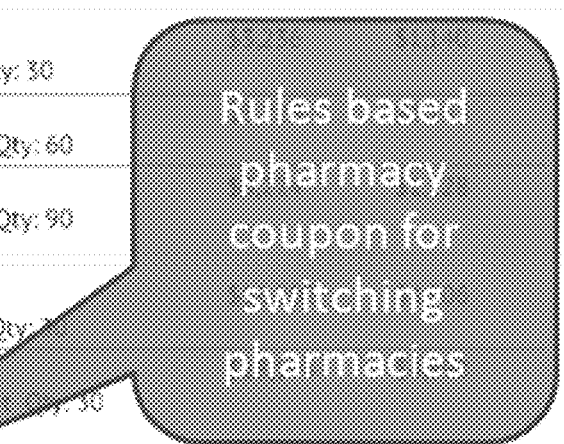

Rules based pharmacy coupon for switching pharmacies

701

Patient's Current Pharmacy:
RiteAid
135 Market St, San Francisco, CA 94102
(415) 555-1212

FIG. 7

Drug Savings Report

Patient: Brown, Danny          Total Savings[1] >$15,000

| Current Medication/Prescriber | Alternative Medication | Annual Total Savings[1] | Annual Patient Savings[2] |
|---|---|---|---|
| Advair Diskus 250mcg-50mcg QTY: 14 Smith, John | Flutica/Salmeterol 232-14 inh QTY: 1 | >$6,500 | >$1,500 |
| Eliquis 5mg Tablet QTY: 60 Smith, John | Warfarin 7.5mg Tab QTY: 30 | >$5,000 | >$375 |
|  | Jantoven 10mg Tab QTY: 30 | >$5,000 | >$375 |
| Crestor 40mg Tab QTY: 30 Smith, John | Simvastatin 80mg Tab QTY: 30 | >$3,000 | >$2,500 |
| Klor-Con 10mEq ER Tab QTY: 30 Smith, John | Klor-Con Sprinkle 10mEq ER Cap QTY: 30 | >$100 | >$100 |
|  | Potassium Cl 10mEq ER Tab QTY: 30 | >$100 | >$100 |
|  | Potassium Cl 10mEq ER Tab QTY: 30 | >$50 | >$50 |

Patient's Preferred Pharmacy:
CVS PHARMACY
5400 YGNACIO VALLEY RD, CONCORD, CA, 94521

[1] Estimated annual total savings (Patient + Payer) based upon current pharmaceutical insurance coverage
[2] Estimated annual patient savings based upon current pharmaceutical insurance coverage

FIG. 8

Drug Savings Report

Patient: Brown, Danny  Total Savings[1] >$15,000

| Current Medication/Prescriber | Alternative Medication | Annual Total Savings[1] | Annual Patient Savings[2] | Patient Copay Credit |
|---|---|---|---|---|
| Advair Diskus 250mcg-50mcg [C] QTY: 14 Smith, John | Fluticas/Salmeterol 232-14 Inh QTY: 1 | >$6,500 | >$1,500 | N/A |
| Eliquis 5mg Tablet [C][P] QTY: 60 Smith, John | Warfarin 7.5mg Tab QTY: 30 | >$5,000 | >$375 | $250 |
| | Jantoven 10mg Tab QTY: 30 | >$5,000 | >$375 | $250 |
| Crestor 40mg Tab [C][P] QTY: 30 Smith, John | Simvastatin 80mg Tab QTY: 30 | >$3,000 | >$2,500 | N/A |
| Klor-Con 10mEq ER Tab [P] QTY: 30 Perkins, Steven | Klor-Con Sprinkle 10mEq ER Cap QTY: 30 | >$100 | >$100 | N/A |
| | Potassium Cl 10mEq ER Tab QTY: 30 | >$100 | >$100 | N/A |
| | Potassium Cl 10mEq ER Tab QTY: 30 | >$50 | >$50 | N/A |

FIG. 9

METHODS AND APPARATUSES FOR PROVIDING ALTERNATIVES FOR PREEXISTING PRESCRIBED MEDICATIONS

CROSS REFERENCE TO RELATED APPLICATIONS

This patent application is a continuation of U.S. patent application Ser. No. 16/036,851, filed Jul. 16, 2018, titled "METHODS AND APPARATUSES FOR PROVIDING ALTERNATIVES FOR PREEXISTING PRESCRIBED MEDICATIONS," now U.S. Patent Application Publication No. 2019/0252049, which claims priority to U.S. Provisional Patent Application No. 62/618,296, filed on Jan. 17, 2018, titled "AUTOMATED ALTERNATIVES ANALYSIS," and U.S. Provisional Patent Application No. 62/645,350, filed Mar. 20, 2018, titled "SYSTEMS AND METHODS FOR AUTOMATED ALTERNATIVES IDENTIFICATION FOR EXISTING PRESCRIPTION DRUGS AND RELATED COSTS." Each of which is herein incorporated by reference in its entirety.

U.S. patent application Ser. No. 16/036,851 also claims priority to U.S. Provisional Patent Application No. 62/667,141, filed on May 4, 2018 (titled "SYSTEMS AND METHODS FOR CONFIGURABLE PRESCRIPTION ALTERNATIVE IDENTIFICATION AND MANAGEMENT/PROVIDER AND PAYER CONFIGURATION ALTERNATIVE DIAGNOSIS USE OF CHOSEN MEDICATIONS"), and U.S. Provisional Patent Application No. 62/670,146, filed May 11, 2018 (titled "AUTOMATED ALTERNATIVES ANALYSIS (AAA) AND DRUG SAVINGS REPORT (DSR)").

INCORPORATION BY REFERENCE

All publications and patent applications mentioned in this specification as of the application filing date of Jul. 16, 2018, for parent application Ser. No. 16/036,851, are herein incorporated by reference in their entirety to the same extent as if each individual publication or patent application was specifically and individually indicated to be incorporated by reference.

FIELD

The methods and apparatuses described herein generally relate to automated modification of existing patient medications and pricing transparency, and more specifically to methods and apparatuses to identify and prioritize alternatives for prescribed medications.

BACKGROUND

Health costs continue to grow in the U.S. and are well documented as a formidable national challenge, with prescription drug costs among the leading sources of cost escalation. Currently, Prescribers are typically notified to renew existing prescriptions for their patients by phone call, fax or electronic systems when an existing prescription has expired, but cost information is generally not provided to the Prescriber, even if the cost of the medication has gone up dramatically and/or lower cost therapeutically equivalent medications are available. Alternative drug or fulfillment cost information is not routinely or automatically delivered to Prescribers or patients related to prescribing new medications or for evaluating the cost-effectiveness of existing medications. Prescribers cannot consider cost-efficiency when prescribing or renewing prescription, or at the point of care. Drug costs and cost savings opportunities are not currently considered for new or existing prescriptions, and as a result drug costs continue to escalate.

For most drug categories there are numerous drug alternatives that a Prescriber might consider in treating a patient. Many Prescribers are not completely familiar with all drugs in every category in which they prescribe. And since Prescribers are given neither a list of alternatives to consider, nor the cost of alternative drugs, both clinical and economic efficiency are lacking.

Drug costs can vary by many factors including: drug chosen, form of drug (long acting, etc.), patient's insurance, patient's deductible, including high deductible plans and Affordable Care Act (ACA) health plans, pharmacy and patient financial assistance programs. Drug costs are dynamic and change regularly, even between new scripts and renewal scripts. Drug costs may also vary depending on the fulfillment means used: e.g., $4 generics (Wal-Mart, Target, etc.), pharmacy discount card or mail order, etc. The pricing of a medication can be complicated.

The optimal alternative drug for a given patient may vary substantially based upon Payer (e.g., insurer, health organizations, etc.) formularies, Payer preferences and provider preferences, or because new drugs are approved or new uses of existing medications are found or approved.

A prescription drug and the pharmacy used to fill the prescription may be selected via an e-Prescribing or electronic health record ("EHR") application. For example, a Prescriber may select the drug to be prescribed. The preferred pharmacy (e.g., a 'pharmacy of last fill') may be a default field in electronic prescribing workflow. The patient's preferred pharmacy is typically entered into the provider's EHR or ePrescribing application when the patient initially registers with the provider for medical care. The prescription may be sent electronically to the patient's chosen pharmacy.

While Prescribers have shown an interest in knowing drug costs, alternative drugs and their costs, and related clinical messages about the prescriptions to be created or renewed, Prescribers typically do not want to spend time considering all possible therapeutic alternatives and then price-shopping for each drug for each patient. Prescribers often have more than one drug in a specific clinical category that they use to treat a specific illness; such as using any of a number of different Statins to treat high cholesterol. Prescribers in these instances could select drugs that are more cost effective for the patient when a prescription is created or renewed if alternative medications and costs were provided.

There is a pressing need for identification and selection of therapeutic drug alternatives for existing medications, ideally at the time and point of care. In addition to addressing other issues in health care, the methods and apparatuses described herein may address this need.

SUMMARY OF THE DISCLOSURE

The present invention relates to methods and apparatuses (e.g., devices, systems, etc., including software, firmware and/or hardware) that may help reduce health care costs, and particularly medication, costs without compromising, and often actually improving, patient care by making care more affordable. For patients taking prescription drugs, these costs can be materially addressed by automatically identifying lower cost therapeutic equivalent alternative drug options in the context of a strategy that is sometimes referred to as "cost transparency" for patients and their care-givers (generically referred to herein as a "patient") and Prescribers, including providers or physicians (generically referred to herein as "Prescribers") triggered by, for example, the Prescribers initiating a new prescription or the patient (e.g., patient care-giver) contacting the Prescriber for an appointment or other care encounters, including telemedicine and patient consultations with Prescribers or providers or Prescribers over electronic systems.

The methods and apparatuses described herein may enable a patient and/or a Prescriber to generate a drug savings report ("DSR") which may identify therapeutic alternatives for existing prescription medications including costs as well as Payer and provider preferences. The DSR may also identify a lower cost pharmacy for the patient to fill existing medications including the ability for pharmacies to insert coupons or rewards into the DSR to motivate patients to change to the new pharmacy.

These methods and apparatuses may increase cost-effective prescribing and thereby lower drug costs. These methods and apparatuses may provide Prescribers and patients more cost-effective, therapeutically equivalent alternatives for existing medications. Specifically, these methods and apparatuses may provide cost-optimized medication and pharmacy alternatives options for existing prescriptions to Prescribers as well as to patients and to Payers (e.g., health plan and other third party care managers and staff) to lower prescription drug costs for Payers and patients. The cost-optimized alternative drug and pharmacy information may be created using the structured methods and apparatuses described herein. Any of these methods may include the creation and delivery of a structured form referred to herein as a drug savings report ("DSR"). These methods and apparatuses may also include rules-based patient financial incentives, reimbursement or rewards (referred to generically herein as incentive credits or, equivalently, as incentive rewards) in order to incentivize the patient and Prescriber to select a lower cost medications meeting rules-based criterion which may be modified or set by a Payer associated with a particular patient.

The structured reporting described herein may be customized, provided, and/or summarized for any of the Payers (e.g., health plans, employers, insurers, etc.) or Prescriber group. These summaries or custom reports may documents the output and impact of the DSRs generated, including: the number of DSR reports generated and delivered; the number of medications changed based upon DSR delivery; the savings resulting from DSR report delivery; and any of these reports may be segregated by patient profile, pharmacy benefit, provider(s), medications, medication categories, alternative presented, savings shown, rewards shown.

For example, typical DSR may be delivered to patients or Prescribers via paper, fax, email or other electronic means including integrated into electronic health record ("EHR") workflow on-demand or triggered automatically at the point of care by patient registration for a care encounter. Prescribers may elect to be reimbursed for their time reviewing medications in the DSR using a Current Procedural Terminology (CPT) codes. In some variations, the DSR may be delivered or made available to patients via paper, fax, email or other electronic means including integrated into patient portals or mobile applications. In some variations, the Payer may receive a DSR and may make it available to the patient and/or Prescriber via a Payer portal. Drug lists used in the DSR may be derived from the patient's record in EHRs and/or Payer pharmacy claims analysis, or directly from the patient.

Patients taking one or more medications may have the opportunity to reduce costs by changing medications or pharmacy fulfillment options based upon their pharmacy benefit coverage. Benefits coverage may change with time as patients change insurers or benefits plans, insurers change formularies, drug costs change, drugs end their patent protection, new medications or uses of medications are approved, etc. There is currently no system to analyze the aggregate drug and pharmacy options for a patient which ideally would be done on a regular basis, and on demand, given the dynamics of the related drug and pharmacy options. Even if patients were to be notified of these options, patients by themselves typically cannot change their medications or move their prescriptions to a lower cost pharmacy without a new prescription from a Prescriber. It is therefore also important to deliver cost-saving options to Prescribers at the proper time in their workflows to empower them to act in a cost-effective manner on behalf of patients and Payers. There are several likely use-cases where the methods and apparatuses (including the use of a DSR) may be particularly helpful. For example, these methods and apparatuses may be used when one or more of patient's current medications require a renewal. In some variations, the methods and apparatuses may be triggered by a patient scheduling an office visit with a Prescriber, such as an annual Medicare physical. Other triggering events that may be beneficial for analyzing a patient's current prescriptions and proposing alternative medications may include the patient asking the Prescriber for assistance in reducing drug costs, the Prescriber undertaking a periodic medication analysis as part of ongoing care management which may be billable to CMS or other Payers; a Prescriber pursuing population health goals by reviewing the medications of some or all of its patient population either at its own initiative or under a contract for periodic review/analysis; and a Payer's clinical staff reviewing the patient's medication list looking for lower cost alternative options. These method and apparatuses may also be useful when a Payer wishes to provide lower cost drug alternative options to their members (e.g., patients) via their member portal, mobile app or in print. In some variations, a Payer may provide existing medication list and/or a DSR to a health information exchange ("HIE"). In some variations, a patient may accesses their medication list via patient portal or mobile app. In some variations, a Payer may wish to send drug cost savings options to a member in print or electronically.

The methods and apparatuses described herein to provide alternatives for one or more preexisting prescribed medications may be triggered as per one of the uses cases above. For example, a trigger may include the patient's current medication list Current medication list is created: by the electronic health record (EHR) for Prescriber-generated requests for alternatives for one or more preexisting prescribed medications. A trigger may include a pharmacy claims analysis for Payer or patient-generated request for alternatives for one or more preexisting prescribed medications.

As will be described in greater detail herein, the list of currently prescribed medications for the patient may be collected from a variety of sources, including patient self-reporting, fulfilled prescription claims (claims analysis), and/or electronic health records. For medication lists created by claims analysis, a Payer may send a pharmacy claims file to a server on a schedule basis. The server, which may be a server (e.g., system) configured to perform the methods described herein, may use the claims file to create patient-specific medication lists for use in the generating the alternatives for one or more preexisting prescribed medications.

In some variations the server may create medication lists for patients from both the Prescriber's EHR and also from Payer claims data then send the Prescriber the compilation of the two for medication reconciliation. The server or other apparatus (e.g., system) performing the methods described herein may take each medication from the list and identify alternative medications to be sent to the patient's Pharmacy Benefit Manager (PBM) for cost analysis; the PBM may respond with costs for the current medication as well as the costs for alternative medications and, if available, lower cost pharmacy. In some variations, the server (or other apparatus) performing the method may interrogate the drug cost transparency response(s) and identify: cost-effective medication alternatives if applicable based upon the PBM response for each current medication; estimated annual patient savings for each lower cost alternative drug or pharmacy; estimated annual Payer savings for each lower cost alternative; rules-based patient shared savings or reward (e.g., incentive credit) to be applied for each lower cost alternative drug or pharmacy; rules-based Payer or 3rd party incentives (e.g., alternative pharmacy offer) for moving some or all medications to an alternative pharmacy, etc.

The server (or other apparatus performing the methods of providing one or more alternatives for one or more preexisting prescribed medications) may perform the methods described herein and assemble the alternative medication and cost information and assemble it into a patient-specific DSR) The server (or other apparatus performing these methods) may deliver the DSR to the intended recipient including: back to the EHR for Prescriber use; to the Payer clinical staff; to the patient via patient portal, mobile app or via print as shown in FIG. 3A; and/or to other authorized third parties, such as contracted and delegated pharmacists, etc. In the EHR use case, the server may integrate with the EHR practice management system to automate billing for Prescribers who use the DSR when Payers offer reimbursement.

The server may be part of a cost managing entity ("managing entity"), and may include a Configurable Alternatives Engine (collectively, a "CAE"). The CAE may include one or more servers or apparatuses, and may perform any of the methods of providing alternatives to prescribed medication described herein. In addition, the CAE may work with EHRs, PBMs and Payers to generate reports related to: the number of DSRs are delivered; the number of alternative drugs or pharmacies are selected; related patient savings; related Payer savings; savings and use of DSR segregated by patient type, pharmacy benefit, drug, alternative drug(s) shown, provider, savings shown, rewards shown, etc.

A CAE may maintain one or more databases for use in providing alternatives a preexisting prescribed medication. For example, a CAE may maintain a database of Payer formularies and rules including preferred drugs ("Payer rules"). This list may be updated regularly (e.g., monthly). The CAE may maintain a list of medications that have been prescribed by each provider with the medications ranked based upon the frequency of the meds being prescribed (e.g., "provider preferred medications"). In some variations, the CAE may include a database of provider-preferred medications that may be ranked based upon Prescriber preferences and/or past prescribing patterns.

For example, a CAE may generate a listing of alternative medications for a patient by collecting (gathering, receiving, inputting, uploading, etc.) one or more medications ("chosen medication" or preexisting medication). The CAE may then identify all therapeutic equivalent drugs ("equivalent medications") that are dose and day's supplied matched from a Therapeutic Equivalency Database. For example, 10 mg of drug A=30 mg of drug B. In another example, drug A is a once/day drug and drug B is a twice/day, so twice as many drug B tabs are equivalent to drug A.

In some variations, the CAE identifies the equivalent medications that are equal or better positioned based upon Payer rules (, e.g., the preferred equivalent medications). If there are less than three preferred equivalent medications, then these medications are sent to the PBM for pricing. If there are more than three preferred equivalent medications, then one may be selected based upon matching to the Prescriber preferred medication list. If more than one is found on this list, then the CAE may select the medication most often prescribed by the Prescriber. If two (or three if no drugs are match to the Prescriber preferred medication list) are selected based upon Payer rules, then the CAE may send up to three preferred equivalent medications to the PBM for pricing. The CAE may receive the PBM responses and eliminates any drugs which are more expensive than the chosen medications (e.g., preexisting medications). The CAE may deliver the cost of the Chosen Medications and the list of lower cost preferred equivalent medications to the Prescriber integrated into EHR workflow either at: the time of prescribing a new medication as a real-time data feed or; at the time of office appointment for existing medications in the form of a DSR.

For example, described herein are methods of providing alternatives for one or more preexisting prescribed medications. Any of these methods may include: receiving a request for an evaluation of a patient's preexisting medications following a triggering event; collecting a set of the patient's preexisting prescribed medications from one or more of: an electronic health record (EHR) associated with the patient and a database of patient pharmacy claims for the patient, and medication information provided by the patient; identifying a plurality of therapeutically equivalent alternative medications corresponding to each of the patient's preexisting prescribed medications in the set based on a clinical equivalency; collecting, from a pharmacy benefit manager (PBM), a cost associated with each of the patient's preexisting prescribed medications, and a cost associated with each of the therapeutically equivalent alternative medications corresponding to each of the patient's preexisting prescribed medications in the set; calculating a patient's savings and a total saving for each of the therapeutically equivalent alternative medications corresponding to each of the patient's preexisting prescribed medications in the set that has a lower cost than the corresponding preexisting prescribed medication; and outputting a DSR showing each of the patient's preexisting prescribed medications, each of the therapeutically equivalent alternative medications corresponding to each of the patient's preexisting prescribed medications that has a lower cost than the corresponding preexisting prescribed medication, and the patient's savings for each of the therapeutically equivalent alternative medications corresponding to each of the patient's preexisting prescribed medications that has a lower cost than the corresponding preexisting prescribed medication.

Any of these methods and apparatuses described herein may alternatively or additionally be configured to incentivize the patient and the Prescriber caring for the patient with shared savings to change to a less expensive medication. For example, any of these methods may determine if a Payer associated with the patient (the Payer is responsible for financing health care services for the patient, such as an insurer or health care cooperative, etc.) has authorized incentive credits, and may automatically calculate incentive credits and offer them to the patient in certain conditions. For example, described herein are methods of providing alternatives for one or more preexisting prescribed medications, the method comprising: receiving a request for an evaluation of a patient's preexisting medications following a triggering event; collecting a set of the patient's preexisting prescribed medications from one or more of: an electronic health record (EHR) associated with the patient and a database of patient pharmacy claims for the patient, and medication information provided by the patient; identifying a plurality of therapeutically equivalent alternative medications corresponding to each of the patient's preexisting prescribed medications in the set based on a clinical equivalency; collecting, from a pharmacy benefit manager (PBM), a cost associated with each of the patient's preexisting prescribed medications, and a cost associated with each of the therapeutically equivalent alternative medications corresponding to each of the patient's preexisting prescribed medications in the set; calculating a patient's savings and a total saving for each of the therapeutically equivalent alternative medications corresponding to each of the patient's preexisting prescribed medications in the set that has a lower cost than the corresponding preexisting prescribed medication; estimating an incentive credit for any therapeutically equivalent alternative medications corresponding to each of the patient's preexisting prescribed medications that has a total savings that is greater than the patient's savings by a predetermined amount when a Payer associated with the patient has authorized incentive credits, wherein the Payer associated with the patient is responsible for financing health care services for the patient; and offering the patient, prescriber or authorized individual, a DSR showing each of the patient's preexisting prescribed medications, each of the therapeutically equivalent alternative medications corresponding to each of the patient's preexisting prescribed medications that has a lower cost than the corresponding preexisting prescribed medication, and the incentive credit for any of the therapeutically equivalent alternative medications corresponding to each of the patient's preexisting prescribed medications that has a lower cost than the corresponding preexisting prescribed medication.

A request for requested DSR may be made manually or automatically. For example, an apparatus (including the server of the CAE) may be configured to automatically begin evaluating the patient's preexisting medications upon detection of a triggering event; the apparatus (e.g., the CAE) may monitor for one or more of the triggering events. For example, the CAE may receive alerts from the patient's EHR or from a Prescriber's appointment calendar, or the like, indicating when the patient has scheduled an appointment.

The CAE may collect (e.g., download, receive, request, gather, etc.) the patient's preexisting prescribed medications, e.g., from one or more of: an electronic health record (EHR) associated with the patient and a database of patient pharmacy claims for the patient, and medication information provided by the patient.

The plurality of therapeutically equivalent alternative medications may refer to medications that are adjusted (e.g., in dosage and/or days supplies) to match the patient's preexisting medication. The CAE may therefore compare a preexisting medication with one or more database(s) (e.g., datastores) of equivalent medications. For example, identifying the plurality of therapeutically equivalent alternative medications based on a clinical equivalency may comprise referencing a database of clinically equivalent alternative medications. Identifying the plurality of therapeutically equivalent alternative medications based on a clinical equivalency may comprise estimating a clinically equivalent dose for each therapeutically equivalent alternative medication, wherein the clinically equivalent dose corresponds to the patient's dose of the corresponding preexisting prescribed medication. in some variations, identifying the plurality of therapeutically equivalent alternative medications based on a clinical equivalency comprises identifying three or more therapeutically equivalent alternative medications, wherein at least two of the therapeutically equivalent alternative medications comprise a Payer preferred equivalent medication and at least one of the therapeutically equivalent alternative medications comprises a Prescriber preferred equivalent medication. A database of therapeutically equivalent alternative medications may therefore be referenced, ranked, sorted, or indexed to include Prescriber preferences, which may be specific to each Prescriber. The same or a different database of therapeutically equivalent alternative medications may therefore be referenced, ranked, sorted, or indexed to include Payer preferences. In some variations a database of therapeutically equivalent alternative medications maybe specific to Payer preferences. In some variations a database of therapeutically equivalent alternative medications maybe specific to Prescriber preferences.

Any of the methods described herein may include contacting the pharmacy benefit manager (PBM) to request costs associated with each of the patient's preexisting prescribed medications, and costs associated with each of the therapeutically equivalent alternative medications corresponding to each of the patient's preexisting prescribed medications in the set. In some variations, the number of inquiries made by the system (e.g., by the CAE) may be minimized or reduced. For example, the number of equivalents for which a cost is requested may be limited to few for each preexisting medication (e.g., 2, 3, 4, 5, 6, 7, etc.).

Any of the methods described herein may output the DSR showing each of the patient's preexisting prescribed medications and each of the therapeutically equivalent alternative medications corresponding to each of the patient's preexisting prescribed medications that have a lower cost than the corresponding preexisting prescribed medication. The output may be visual, e.g., it may be a written report on paper, on a screen (e.g., on a display of a laptop, tablet, smartphone, etc.), or the like. The report may include the patient's savings for each of the therapeutically equivalent alternative medications corresponding to each of the patient's preexisting prescribed medications that have a lower cost than the corresponding preexisting prescribed medication; in some variations, the report also includes the total savings (e.g., the savings to the Payer). Outputting the DSR may include providing the DSR to the Prescriber and the patient.

Any of the methods and apparatuses described herein may include rank-ordering the therapeutically equivalent alternative medications prior to collecting the cost, based upon rules specific to a Payer, and identifying which of the alternative medications is of equal or greater preference. For example, the same or a different database (datastore) may include rules or other rankings specific to the Payer. The rules specific to the Payer may include one or more of: formularies, preferred medications and excluded medications.

Any of the method and apparatuses described herein may include estimating an incentive credit for any therapeutically equivalent alternative medications corresponding to each of the patient's preexisting prescribed medications that have a total savings that is greater than the patient's savings by a first predetermined amount and including the incentive credit on the DSR. For example, an incentive credit may be calculated as one or more of: a percentage of the difference between the total savings and the patient's savings, a fixed amount, or a tiered amount. In some variations, the first predetermined amount is selectable by the Payer (e.g., $200, $300, $400, $500, $600, $700, $800, etc.).

In any of the methods and apparatus variations described herein, calculating the patient's savings and the total savings may comprise calculating the annual patient's savings and the annual total savings.

Any appropriate triggering event may be used. For example, the triggering event may be one or more of: the patient has a scheduled appointment with the Prescriber; the Prescriber requests evaluation of existing patient medications; the patient request evaluation of existing medications; the Payer requests evaluation of existing patient medications. In some variations, the triggering event is a scheduled appointment with the Prescriber.

Collecting the cost associated with each of the patient's preexisting prescribed medications and the cost associated with each of the therapeutically equivalent alternative medications corresponding to each of the patient's preexisting prescribed medications in the set may include the cost associated with each of the patient's one or more preexisting prescribed drugs and the one or more alternative drugs at an alternative pharmacy in proximity to the patient.

Although the methods and apparatuses described herein may review and propose alternatives to all or many of a patient's preexisting medication, in some variations these methods and apparatuses may be configured to determine alternatives to just one (or at least one) or a subset of the patient's preexisting prescribed medications. For example a method of providing alternatives a preexisting prescribed medication may include: receiving a request for an evaluation of a patient's preexisting medication following a triggering event; identifying the patient's preexisting prescribed medication from one or more of: an electronic health record (EHR) associated with the patient and a database of patient pharmacy claims for the patient, and medication information provided by the patient; identifying a plurality of therapeutically equivalent alternative medications corresponding to the preexisting prescribed medication based on a clinical equivalency; collecting, from a pharmacy benefit manager (PBM), a cost associated with the preexisting prescribed medication, and a cost associated with each of the therapeutically equivalent alternative medications; calculating a patient's savings and a total saving for each of the therapeutically equivalent alternative medications that has a lower cost than the preexisting prescribed medication; and outputting a DSR showing the preexisting prescribed medication, each of the therapeutically equivalent alternative medications that has a lower cost than the preexisting prescribed medication, and the patient's savings for each of the therapeutically equivalent alternative medications that has a lower cost than the corresponding preexisting prescribed medication.

Also described herein are apparatuses configured to perform any of the methods described herein. For example, described herein are systems for providing alternative for one or more of a patient's preexisting prescribed medications. These systems may generally include one or more processors and a memory coupled to the one or more processors that is configured to store computer-program instructions that, when executed by the one or more processors, perform a computer-implemented method. For example, described herein are systems for providing alternatives for one or more of a patient's preexisting prescribed medications that include: one or more processors; and a memory coupled to the one or more processors, the memory configured to store computer-program instructions, that, when executed by the one or more processors, perform a computer-implemented method comprising: receiving, in the one or more processors, a request for an evaluation of a patient's preexisting medications following a triggering event; collecting a set of the patient's preexisting prescribed medications from one or more of: an electronic health record (EHR) associated with the patient and a database of patient pharmacy claims for the patient, and medication information provided by the patient; identifying a plurality of therapeutically equivalent alternative medications corresponding to each of the patient's preexisting prescribed medications in the set based on a clinical equivalency; collecting, from a pharmacy benefit manager (PBM), a cost associated with each of the patient's preexisting prescribed medications, and a cost associated with each of the therapeutically equivalent alternative medications corresponding to each of the patient's preexisting prescribed medications in the set; calculating a patient's savings and a total saving for each of the therapeutically equivalent alternative medications corresponding to each of the patient's preexisting prescribed medications in the set that has a lower cost than the corresponding preexisting prescribed medication; and outputting a DSR showing each of the patient's preexisting prescribed medications, each of the therapeutically equivalent alternative medications corresponding to each of the patient's preexisting prescribed medications that has a lower cost than the corresponding preexisting prescribed medication, and the patient's savings for each of the therapeutically equivalent alternative medications corresponding to each of the patient's preexisting prescribed medications that has a lower cost than the corresponding preexisting prescribed medication.

For example, a system for providing alternatives for one or more of a patient's preexisting prescribed medications may include: one or more processors; and a memory coupled to the one or more processors, the memory configured to store computer-program instructions, that, when executed by the one or more processors, perform a computer-implemented method comprising: receiving a request for an evaluation of a patient's preexisting medications following a triggering event; collecting a set of the patient's preexisting prescribed medications from one or more of: an electronic health record (EHR) associated with the patient and a database of patient pharmacy claims for the patient, and medication information provided by the patient; identifying a plurality of therapeutically equivalent alternative medications corresponding to each of the patient's preexisting prescribed medications in the set based on a clinical equivalency; collecting, from a pharmacy benefit manager (PBM), a cost associated with each of the patient's preexisting prescribed medications, and a cost associated with each of the therapeutically equivalent alternative medications corresponding to each of the patient's preexisting prescribed medications in the set; calculating a patient's savings and a total saving for each of the therapeutically equivalent alternative medications corresponding to each of the patient's preexisting prescribed medications in the set that has a lower cost than the corresponding preexisting prescribed medication; estimating an incentive credit for any therapeutically equivalent alternative medications corresponding to each of the patient's preexisting prescribed medications that has a total savings that is greater than the patient's savings by a predetermined amount when a Payer associated with the patient has authorized incentive credits, wherein the Payer associated with the patient is responsible for financing health care services for the patient; and offering the patient, prescriber or authorized individual, a DSR showing each of the patient's preexisting prescribed medications, each of the therapeutically equivalent alternative medications corresponding to each of the patient's preexisting prescribed medications that has a lower cost than the corresponding preexisting prescribed medication, and the incentive credit for any of the therapeutically equivalent alternative medications corresponding to each of the patient's preexisting prescribed medications that has a lower cost than the corresponding preexisting prescribed medication. A system for providing alternatives for a preexisting prescribed medication, the system comprising: one or more processors; and a memory coupled to the one or more processors, the memory configured to store computer-program instructions, that, when executed by the one or more processors, perform a computer-implemented method comprising: receiving a request for an evaluation of a patient's preexisting medication following a triggering event; identifying the patient's preexisting prescribed medication from one or more of: an electronic health record (EHR) associated with the patient and a database of patient pharmacy claims for the patient, and medication information provided by the patient; identifying a plurality of therapeutically equivalent alternative medications corresponding to the preexisting prescribed medication based on a clinical equivalency; collecting, from a pharmacy benefit manager (PBM), a cost associated with the preexisting prescribed medication, and a cost associated with each of the therapeutically equivalent alternative medications; calculating a patient's savings and a total saving for each of the therapeutically equivalent alternative medications that has a lower cost than the preexisting prescribed medication; and outputting a DSR showing the preexisting prescribed medication, each of the therapeutically equivalent alternative medications that has a lower cost than the preexisting prescribed medication, and the patient's savings for each of the therapeutically equivalent alternative medications that has a lower cost than the corresponding preexisting prescribed medication.

Also described herein are non-transient, computer-readable medium containing program instructions for providing alternatives for a preexisting prescribed medication, the program instructions causing a processor to perform any of the methods described herein.

In some variations, the DSRs (or a modified version of the report) described herein are configured to be provided to the patient's physician or health care Prescriber. For example, in some variations described herein are methods and apparatuses for generating one or more reports for auditing and/or reconciling a patient's medications. Thus in some variations, the reports may identify the patient's preexisting prescribed medications from one or more of: an electronic health record (EHR) associated with the patient and a database of patient pharmacy claims for the patient, and medication information provided by the patient, and generate a report that indicates from where each of these medications was identified. As mentioned above, the list of existing medications can come from the EHR or the Payer, or both. If available from both sources the DSR can identify which listed drugs come from which source and allow the patient and/or Prescriber to compare the lists sometimes known as medication reconciliation.

The DSR can be created and used by Prescribers integrated into their EHR workflows and triggered by patient appointments or on an ad hoc basis. The DSR can be created and used by patients via patient portals or mobile applications. The DSR can be created and used by the Payer staff or sent from the Payer to the patient using print or electronic means.

As used herein, the term prescription is defined broadly herein to include drugs, medications, compounds, vaccines, medical devices, therapies, or anything a Prescriber can order for a patient.

The systems and methods disclosed herein can include coordination from Prescribers or Prescribers, Payers, patients, and pharmacies. The systems and methods may not only reduce the cost of prescription, but may also benefit a patient by increasing adherence to medication and preventing delayed onset of care. These systems and methods may further enable a Prescriber to spend a fixed amount of time assisting the patient with lowering drug costs and provide this service when the patient is being seen for an appointment and/or the Prescriber's time is being reimbursed.

The systems and methods described herein can allow the Prescriber and/or the patient the ability to automatically query the patient's PBM using a configurable rules-based engine triggered by a patient encounter such as an office visit or prescription renewal request, and give the Prescriber curated or prioritized lower cost therapeutic equivalent options to consider at the time of the encounter. The system and method can enable a Prescriber to discuss less expensive drug and fulfillment options with their patients and change medication or fulfillment options at the time of appointments and care encounters.

The systems and methods described herein may calculate the annual savings to the patient and to the Payer that would be achieved by substituting a lower cost alternative medication for an existing medication and present this information to the Prescriber and/or the patient. They may also take the total savings potential represented by all alternative drugs and provide the patient and/or Prescriber with an estimate of the total potential savings achievable by using all available lower cost alternatives. The system and method can also create additional financial incentives that benefit the patient associated to substituting a lower cost medications by taking a predetermined portion of the Payer savings and delivering it to the patient in the form of a credit or copay reduction (e.g., "reward" or "credit"). This redemption of the reward can be affected either electronically via the system and method's communication with the Payer's claims processor and/or via a printable coupon rewards coupon provided to the patient.

For example, the systems and methods described herein may use an internal proprietary configurable database and rules engine to identify potential lower cost alternative drugs that the Prescriber might consider in treating the patient. The system and method can rank or prioritize these alternatives based upon Payer formularies and preferences, drug costs, diagnosis treated and Prescriber preferences. The system and method can determine the patient's pharmacy benefits manager ("PBM") and sends predetermined data regarding the patient and the Prescriber to the patient's PBM requesting specific pricing and information related to lower cost medications. The system and method can further deliver to the Prescriber at the point of care in the EHR and/or patient via print or electronic medium including the EHR patient portal the exact cost of each relevant alternative drug inclusive of total drug costs as well as the patient's out-of-pocket costs inclusive of patient's insurance, deductibles, copays and other relevant factors.

For example, described herein are methods of providing alternatives for one or more preexisting prescribed medications that include: receiving a request for an evaluation of a patient's preexisting medications following a triggering event; collecting a set of the patient's preexisting prescribed medications (e.g., from one or more of: an electronic health record (EHR) associated with the patient, a database of pharmacy claims for the patient, and medication information provided by the patient or a combination of these sources); identifying a plurality of therapeutically equivalent alternative medications corresponding to the patient's preexisting prescribed medications in the set based on a clinical equivalency (which may include initially identifying larger number of alternatives per pre-existing medication and reducing the number down, e.g., by rank-ordering them based on Payer and/or Prescriber criteria and/or other criteria); collecting, from a pharmacy benefit manager (PBM), a patient cost and a total cost associated with the patient's preexisting prescribed medications and with each of the therapeutically equivalent alternative medications corresponding to the patient's preexisting prescribed medications in the set; calculating a patient's savings and a total saving for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication; and offering the patient, prescriber or other authorized individual, in a drug savings report (DSR), alternatives for the patient's preexisting prescribed medications, wherein the DSR shows: the patient's savings for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication.

A method of providing alternatives for one or more preexisting prescribed medications may include: receiving a request for an evaluation of a patient's preexisting medications following a triggering event; collecting a set of the patient's preexisting prescribed medications from one or more of: an electronic health record (EHR) associated with the patient and a database of patient pharmacy claims for the patient, and medication information provided by the patient; identifying a plurality of therapeutically equivalent alternative medications corresponding to each of the patient's preexisting prescribed medications in the set based on a clinical equivalency; collecting, from a pharmacy benefit manager (PBM), a patient cost and a total cost associated with each of the patient's preexisting prescribed medications, and a patient cost associated and a total cost associated with each of the therapeutically equivalent alternative medications corresponding to the patient's preexisting prescribed medications in the set; calculating a patient's savings and a total saving for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication; estimating an incentive credit for any therapeutically equivalent alternative medication that has a total savings that is greater than the patient's savings by a predetermined amount when a payer associated with the patient has authorized incentive credits, wherein the payer associated with the patient is responsible for financing health care services for the patient; and offering the patient, prescriber or authorized individual, in a drug savings report (DSR) any incentive credit for each of the therapeutically equivalent alternative medication corresponding to the preexisting prescribed medication, wherein the DSR shows: each of the patient's preexisting prescribed medications, any therapeutically equivalent alternative medications corresponding to each of the patient's preexisting prescribed medications that have a lower patient cost, a lower total cost or both a lower patient cost and total cost than the corresponding preexisting prescribed medication, and any incentive credit for each of the therapeutically equivalent alternative medications corresponding to the preexisting prescribed medication.

A method of providing alternatives for a preexisting prescribed medication may include: receiving a request for an evaluation of a patient's preexisting medication following a triggering event; identifying the patient's preexisting prescribed medication from one or more of: an electronic health record (EHR) associated with the patient and a database of patient pharmacy claims for the patient, and medication information provided by the patient; identifying a plurality of therapeutically equivalent alternative medications corresponding to the preexisting prescribed medication based on a clinical equivalency; collecting, from a pharmacy benefit manager (PBM), a patient cost and a total cost associated with the preexisting prescribed medication and each of the therapeutically equivalent alternative medications; calculating a patient's savings and a total saving for each of the therapeutically equivalent alternative medications that has a lower cost than the preexisting prescribed medication; estimating an incentive credit for any therapeutically equivalent alternative medication that has a total savings that is greater than the patient's savings by a predetermined amount when a payer associated with the patient has authorized incentive credits, wherein the payer associated with the patient is responsible for financing health care services for the patient; and offering the patient, prescriber or authorized individual, in a drug savings report (DSR), alternatives for the patient's preexisting prescribed medication, wherein the DSR shows: the therapeutically equivalent alternative medications, any patient's savings for each of the therapeutically equivalent alternative medications, and any incentive credit for each of the therapeutically equivalent alternative medication.

Thus, any of the methods described herein may include rank-ordering the therapeutically equivalent alternative medications prior to collecting the patient cost and total cost, e.g., based upon rules specific to a payer, and identifying which of the alternative medications is of equal or greater preference. For example, the rules specific to the payer may include one or more of: formulary tiers, preferred medications, and excluded medications. The method may also include removing, from the plurality of therapeutically equivalent alternative medications corresponding to the patient's preexisting prescribed medications, any therapeutically equivalent alternative medications below a threshold rank. For example, the total number of alternatives per preexisting medication may be limited (e.g., to 1, 2, 3, 4, 5, etc.); the top ranked alternatives may include one or more preferences from the payer and one or more preferences from the prescriber (these preferences may be different).

Identifying the plurality of therapeutically equivalent alternative medications based on the clinical equivalency may include referencing a database of clinically equivalent alternative medications. Identifying the plurality of therapeutically equivalent alternative medications based on the clinical equivalency may include estimating a clinically equivalent dose for each therapeutically equivalent alternative medication, wherein the clinically equivalent dose corresponds to the patient's dose of the corresponding preexisting prescribed medication.

As mentioned, identifying the plurality of therapeutically equivalent alternative medications based on the clinical equivalency may include identifying three or more therapeutically equivalent alternative medications, wherein at least two of the therapeutically equivalent alternative medications comprise a payer preferred equivalent medication and at least one of the therapeutically equivalent alternative medications comprises a prescriber preferred equivalent medication.

In general, any of these methods may include estimating an incentive credit for any therapeutically equivalent alternative medication (e.g., estimating an incentive credit for any alternative that has a total savings that is greater than the patient's savings by a first predetermined amount), and including the incentive credit in the offer (e.g., on the DSR). For example, the incentive credit may be calculated as one or more of: a percentage of the difference between the total savings and the patient's savings, a fixed amount, or a tiered amount. The first predetermined amount may be selectable by the payer. Any of these methods may include providing the DSR to the prescriber, patient or other authorized individual or organization.

The DSR may also show the total savings for each of the therapeutically equivalent alternative medications corresponding to each of the patient's preexisting prescribed medications that has a lower cost than the corresponding preexisting prescribed medication. The patient's savings and the total savings may be annual patient's savings and/or annual total savings.

The rules specific to the payer may include minimum threshold amounts to present the alternative medication for one or more of: patient cost savings and total savings. In cases where the patient cost savings and/or total savings are less than a minimum threshold for display, these alternative medications may not be included in the offer (e.g., the DSR).

Collecting the patient cost and total cost may include collecting a patient cost and total cost associated with each of the patient's one or more preexisting prescribed drugs and the one or more alternative drugs at an alternative pharmacy.

Also described herein are systems for performing any of the methods described. Any of these systems (e.g., systems for providing alternatives for one or more of a patient's preexisting prescribed medications) may include: one or more processors; and a memory coupled to the one or more processors, the memory configured to store computer-program instructions, that, when executed by the one or more processors, perform a computer-implemented method comprising any of the methods described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7 is another example of a DSR.
FIG. 8 is another example of a DSR.
FIG. 9 is another example of a DSR.

DETAILED DESCRIPTION

The methods and apparatuses described herein may be implemented by a CAE in order to provide alternatives for one or more preexisting prescribed medications. For example a DSR ("DSR") may provide an analysis of existing medications taken by a patient and provides lower cost therapeutic equivalent alternative medications based upon the patient's pharmacy coverage details. The alternative medications may be identified by a CAE that may perform any of the methods described herein. The patient's medication list may be obtained from an electronic health record ("EHR"), Payer claims data, and/or patient self reporting. The DSR may empower Prescribers and patients to consider lower cost medications by delivering the DSR to Prescribers integrated into EHRs at the point/time of care. In some variation, the patient's may be incentivized by receiving rewards or credits when the total saving (which may normally be realized primarily by the Payer) is substantial, particularly as compared with the patient's savings alone. The DSR creation and delivery may be triggered by an actual or scheduled patient encounter with their Prescriber.

The DSR may also be delivered to patients in a member or patient portal, mobile app or by print. In some variations, the DSR may be delivered to a health information exchange ("HIE"). In some variations, the report may be delivered to Payer staff such as pharmacists or therapeutic interchange clinicians. The patient's medication list may be obtained using Payer claims.

Figure 1A:
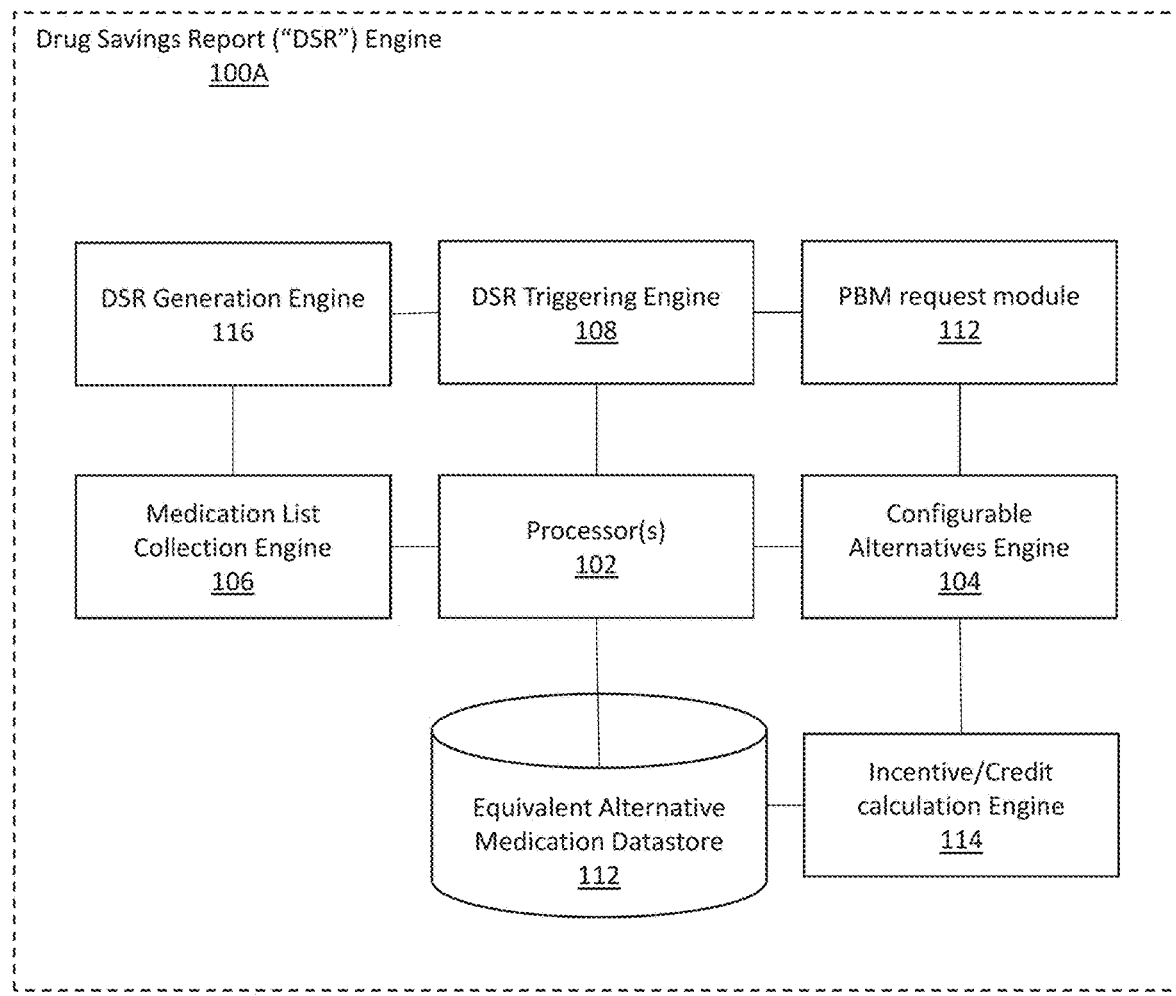
FIG. 1A is a diagram showing an example of the DSR Engine system.
Figure 1B:
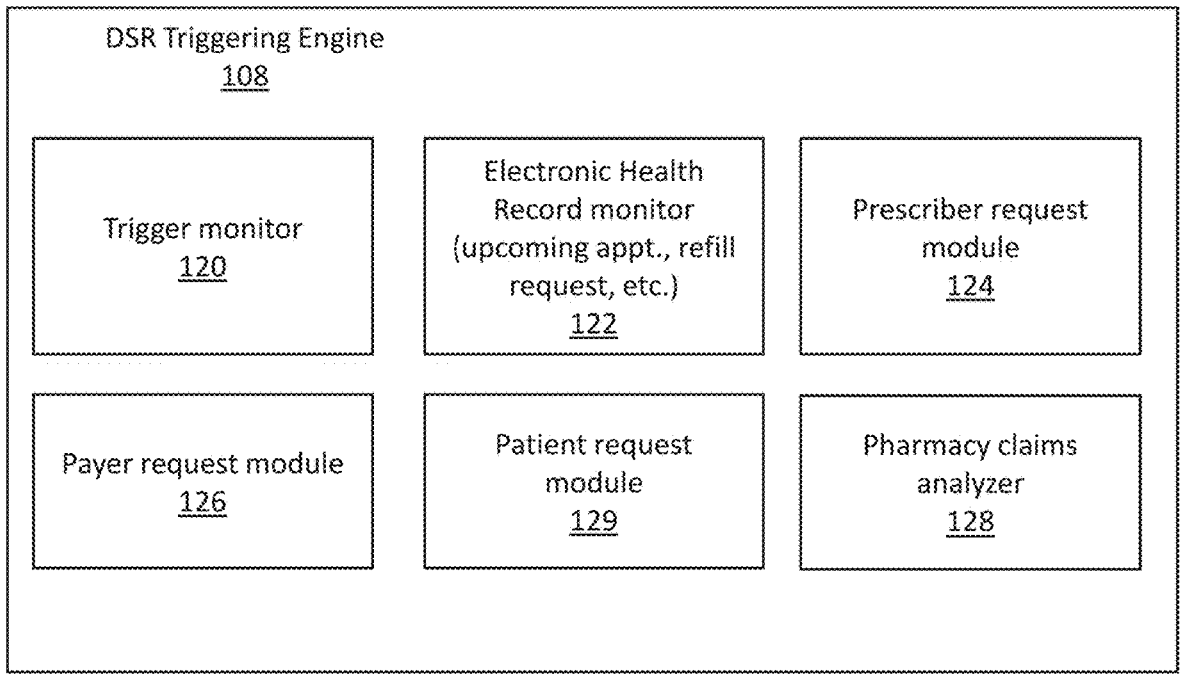
FIG. 1B is a diagram showing an example of an automated evaluation request trigger engine.
Figure 1C:
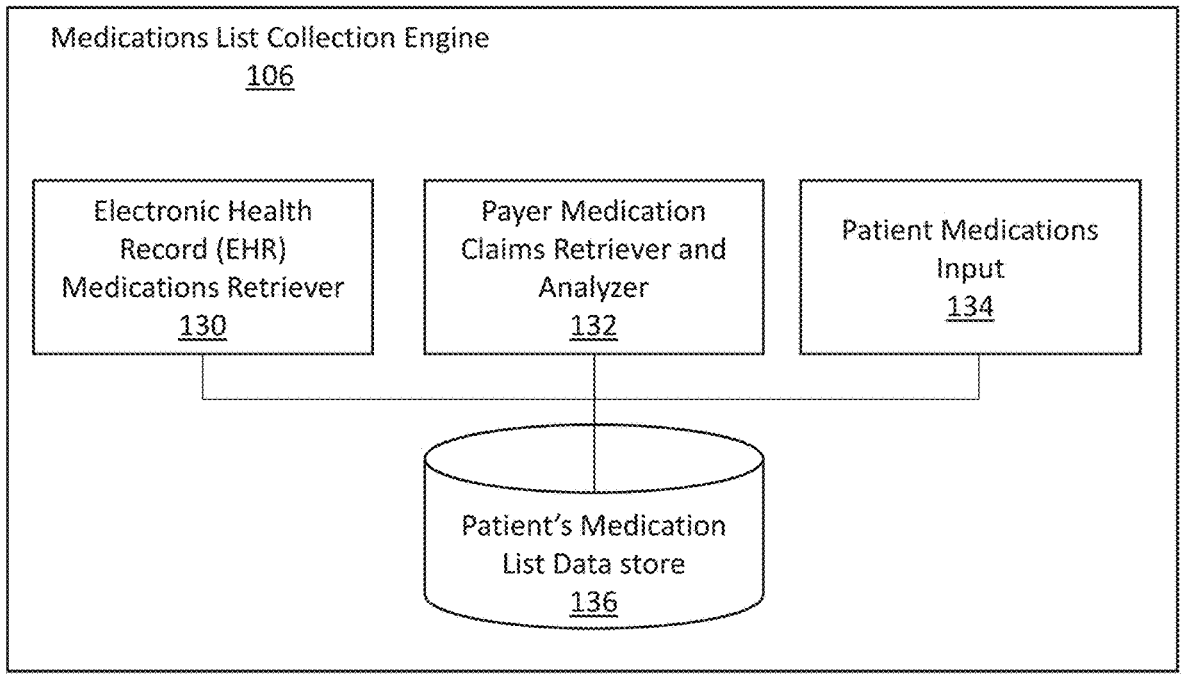
FIG. 1C is a diagram showing an example of an automated Medications List Collection Engine.

FIG. 1A is an example of a diagram showing an example of a DSR Engine (System 100A. The modules of the DSR Engine 100A may include one or more engines and datastores. A computer system can be implemented as an engine, as part of an engine or through multiple engines. As used herein, an engine includes one or more processors 102 or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The DSR Engine (System 100A may include a computer-readable medium (not shown) that may execute on one or more processors 102, a Configurable Alternatives Engine 104, Medication List Collection engine 106, an evaluation request trigger engine, an Therapeutic Equivalency Database 140, an PBM Request Module 112, an Incentive/Credit Calculation Engine 114, and a DSR Generating Engine 116. The computer-readable medium may include any computer-readable medium, including without limitation a bus, a wired network, a wireless network, or some combination thereof. These modules (engines, datastores, etc.) may be connected to each other in any combination/sub-combination and may be arranged to generate alternatives for one or more preexisting prescribed medications, including generating a report (such as a PSR).

The DSR Triggering Engine 108 may include a trigger monitor (monitoring module) that may be configured to receive input from each of the electronic health record monitor 112, the Payer request module 126 the Prescriber request module 124 and the pharmacy claims analyzer 128. For example, the electronic health record monitor 112 may monitor a patient's electronic health record (or in some variations a number of different patients/members EHRs) to detect an upcoming appointment with a Prescriber, a refill for a prescription request, etc. The EHR monitor 112 may then signal the trigger monitor 120 that such an event has occurred from the EHR, and may pass information including the patient ID/name, date of the appointment/request, and any other additional information. Similarly, the Prescriber request module 124 may monitor the Prescribers' electronic records to detect a triggering event, such as a medication reconciliation, an appointment for the patient, or a manual request for providing alternatives for one or more preexisting prescribed medications, etc. The Payer request module 126 may monitor the Payer's electronic records to detect a triggering event, and/or may receive a manual request for providing alternatives for one or more preexisting prescribed medications, a regularly scheduled review and analysis of the patient's preexisting prescribed medicines, etc. In some variations, the DSR Triggering Engine 108 may also include a patient request module 129 that may retrieve a patient-generated request for an analysis of the patient's current (preexisting) medicines to generate alternatives for one or more preexisting prescribed medications. In addition, the DSR Triggering Engine 108 may also include a Pharmacy Claims Analyzer 128 that may review pharmacy claims to determine a patient's medication list for use in the Drug Savings Report 120.

The Medications List Collection Engine 106 may generate a collection (e.g., list, report, tally, set, etc., which may be sorted or unsorted) of the patient's preexisting prescribed medications. The Medications List Collection Engine 106 may collect this information from the patient's electronic health records via an Electronics Health Record (EHR) Medications Retriever 130. Alternatively or additionally, the Collection engine 106 may retrieve preexisting prescribed medication information from the patient's paid pharmacy claims via the Payer Medication Claims Retriever and Analyzer 132. In addition, the patient may themselves report medications via a Patient Medications Input 134, which may provide a user interface for entering medications and may be part of the Configurable Alternatives Engine System, or may be part of another system, including a Prescriber, pharmacy and/or Payer system into which the patient enters one or more medications. The patient Medications List Collection Engine may include one or more datastores, including a Patient Prescribed Medications Datastore 136, into which prescribed patient medications may be stored, retrieved and/or updated. Note that in general the preexisting prescribed medications may include the identity of the medication (e.g., name) as well as patient dosage information (the dose form, the dose concentration, the times/day that the medication is to be taken, etc.).

Figure 1D:
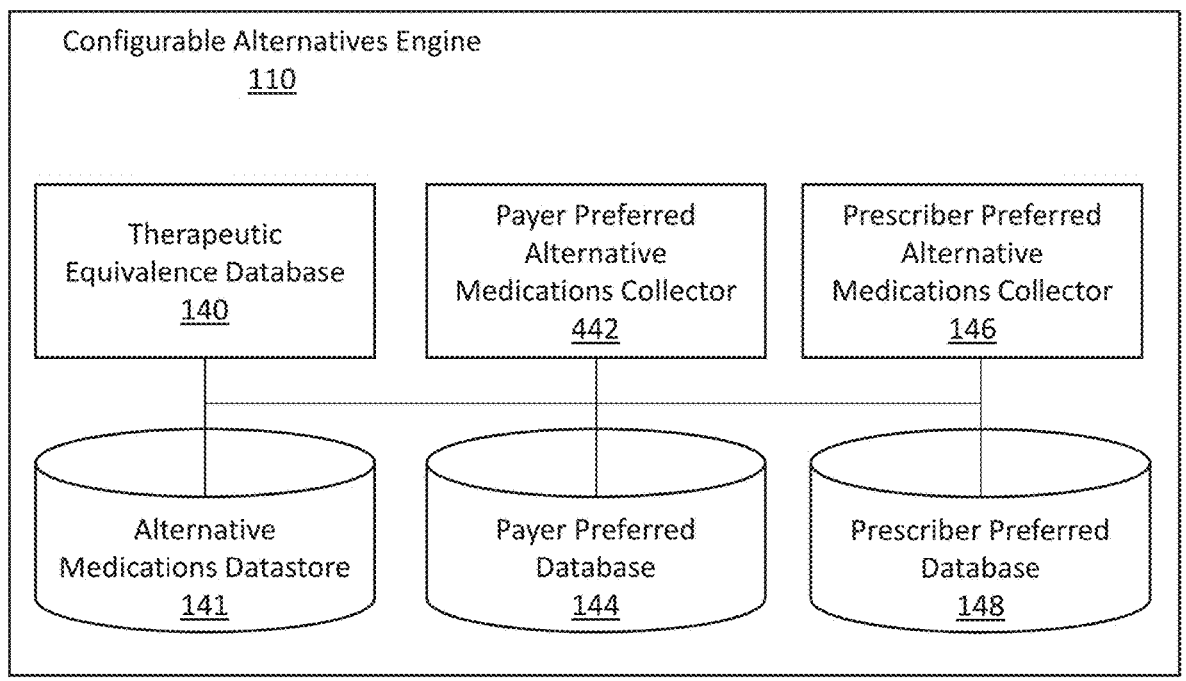
FIG. 1D is a diagram showing an example of an automated Equivalent Alternative Medicine Finder.

FIG. 1D illustrates one example of a Configurable Alternatives Engine 110 for finding equivalent alternative medicines. In this example, the CAE (e.g., "finder" 110) includes a Therapeutic Equivalency Database 140 as well as input from one or more sources, such as a Payer Preferred Alternative Medications Collector 442 and/or a Prescriber Preferred Alternative Medications Collector 146. For example, the Payer Preferred Alternative Medicines Collector may retrieve, update, and/or manage a database of Payer Preferred Alternative Medications (e.g., "Payer Preferred Database 144); these alternative medications in this database may be sorted or ranked. The Prescriber Preferred Alternative Medicines Collector may retrieve, update, and/or manage a database of Prescriber Preferred Alternative Medications (e.g., "Prescriber Preferred Database 148); these alternative medications in this database may be sorted or ranked. In some variations, the Configurable Alternatives Engine 110 may use a database to cross-reference the preexisting medications with a listing of Alternative Medications in the Therapeutic Equivalency Database 140. Alternatives may be prioritized using the Payer Preferred Alternative Medications Database 144 and/or prioritized using the Prescriber Preferred Database 148.

Figure 2:
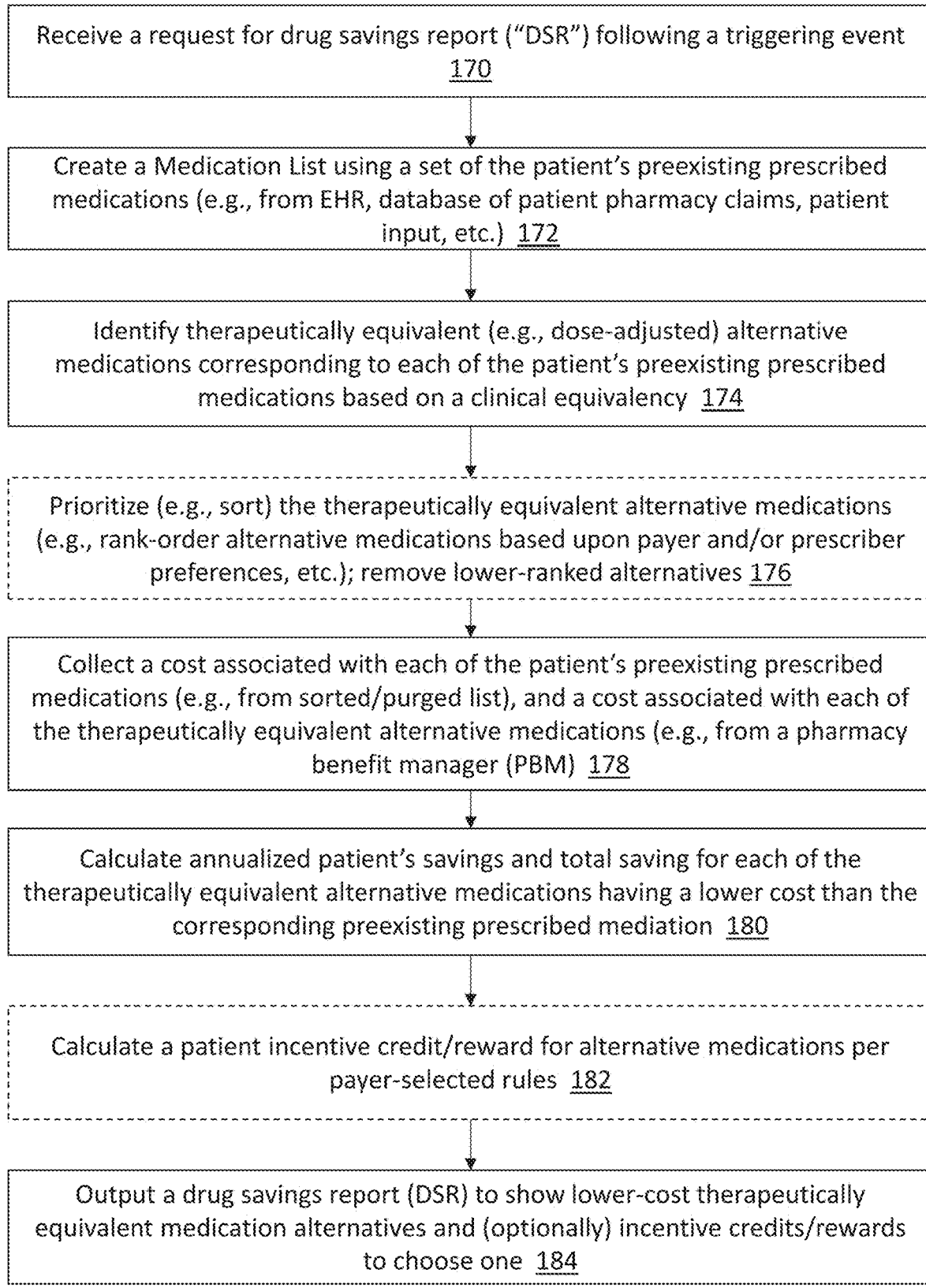
FIG. 2 is a flowchart of an example of a method of providing alternatives for one or more preexisting prescribed medications.

FIG. 2 illustrate one example of a method of providing alternatives for one or more preexisting prescribed medications; this method, or a variation as described herein, may be performed by one or more apparatuses, e.g., by a CAE. The method may include receiving a request for an evaluation of a patient's preexisting medications following a triggering event 170. As mentioned above, any appropriate triggering event may be automatically or manually detected. Following a manual or automatic triggering, a collection (e.g., set, group, listing) of one or more of the patient's preexisting prescribed medications may be collected, e.g., from one or more of: an electronic health record (EHR) associated with the patient and a database of patient pharmacy claims for the patient, and medication information provided by the patient 172. A plurality of therapeutically equivalent alternative medications corresponding to each of the patient's preexisting prescribed medications in the set may then be identified, e.g., based on a clinical equivalency 174. This step may include determining a dose equivalence for each of the equivalent alternative medications, so that the therapeutically equivalent alternative medications each have an equivalent dose, e.g., dose form, concentration, dosing regimen/timing (doses/day). The therapeutically equivalent medications may be collected together in a set that includes the preexisting prescribed medication and/or the dosage information for each of the preexisting prescribed medication and the therapeutically equivalent medication. Optionally, the method may include prioritizing (e.g., sorting) the therapeutically equivalent alternative medications for each preexisting medication. Prioritizing may include ranking, sorting, and/or organizing the alternative medications 176. In some variations this may include reduce the number of alternative medications (e.g., down to 2 or less, 3 or less, 4 or less, 5 or less, etc.), and/or selecting Prescriber preferred and/or Payer preferred medications. For example, the collection of therapeutically equivalent alternative medications may be sorted so that medications based on those that are preferred by the Payer ("Payer preferred medications") and/or preferred by the Prescriber ("Prescriber preferred"). Payer and/or Prescriber preferences may be determined or indicated at the source (e.g., in a database of Payer preferred equivalents and/or prescribed preferred equivalents, etc.). The alternative medications may be ranked in order of the preference for the Payer based upon Payer rules, which may include, for example, the formulary and preferred medications and identifying which, if any, of the alternative medications is of equal or greater preference by the Payer ("Payer-preferred Equivalent Medications"). Similarly, the Prescriber-preferred medications may be determined, e.g., from a listing of Prescriber-preferred medications. Any of the Payer-Preferred Equivalent Medications which are Prescriber-preferred Medications may also be determined, and, if so, medications most often prescribed that are also Prescriber-preferred Medications (as prescribed by the Provide and referred to herein as Payer/Prescriber-preferred Equivalent Medication") may be determined. This information may be used to reduce the list of therapeutically equivalent alternative medications. For example, the collection of therapeutically equivalent alternative medications may be selected so that at least one of the alternative medications is a Prescriber-preferred alternative medication and at least one of the alternative medications is a Payer-preferred alternative medication. In some variations all of the alternative medications are Payer-preferred alternative medications. For example, the method may include identifying a combination of three Payer-preferred Equivalent medications at last or exactly one of which is also the most commonly prescribed Payer/Prescriber-preferred Equivalent Medication (if one exists). Thus, in any of these variations, the therapeutically equivalent alternative medications may be a collection of alternative medications that are limited to those Payer-preferred and/or prescribed preferred medications and/or limited to a subset (e.g., the top x alternative medications, where x is, for example, 2, 3, 4, 5, 6, 7, 8, 9, 10, etc.).

Any of these methods may then include collecting, from a pharmacy benefit manager (PBM), a cost associated with each of the patient's preexisting prescribed medications (e.g., from the set of x therapeutically equivalent prescribed medication), and a cost associated with each of the therapeutically equivalent alternative medications corresponding to each of the patient's preexisting prescribed medications in the set 178.

Any of these methods may also include calculating a patient's savings and a total saving for each of the therapeutically equivalent alternative medications corresponding to each of the patient's preexisting prescribed medications in the set that has a lower cost than the corresponding preexisting prescribed medication 180. This is described in greater detail herein, but may be estimated from a database of alternative medicines.

Optionally, in some variations, the method may include calculating an incentive credit/reward for alternative medications having a total saving greater than the patient savings. The incentive credit/reward may be an option that is selectable by the Payer. For example, the Payer may elect to share the total cost saving with the patient or not. The Payer may set the threshold for determining when an incentive cash/reward is to be calculated and offered (e.g., y dollars, such as $1, $50, $100, $200, $250, $300, $500, $700, $750, $800, $900, $1000, etc.). The Payer may also set or select the amount and/or type of incentive credit/reward. The reward may be a fixed amount (e.g., a single flat fee reward, a tranched or tiered reward system based on the amount of the difference between the total savings and the individual savings 182.

Finally, the method may present (e.g. output) a DSR to a user and/or a Prescriber and/or the Payer. For example, the method may include outputting a DSR showing each of the patient's preexisting prescribed medications, each of the therapeutically equivalent alternative medications corresponding to each of the patient's preexisting prescribed medications that has a lower cost than the corresponding preexisting prescribed medication, and the patient's savings for each of the therapeutically equivalent alternative medications corresponding to each of the patient's preexisting prescribed medications that has a lower cost than the corresponding preexisting prescribed medication 184.

In some variations, the DSR Engine is comprised of four logical components: Therapeutic Equivalency Database, Payer Preferences Database, Provider Preferences Database, and Configurable Alternatives Engine software. The Therapeutic Equivalency Database may be the Prescription alternative identification and management data repository used to store clinical content. Therapeutic Equivalency Database is used by the Configurable Alternatives Engine to identify clinically appropriate, dose adjusted, alternative medications and corresponding medication Quantities and Days' Supply. Therapeutic Equivalency Database supports the following: identification of whether a medication is recognized as Multi-Source or Single Source, identification of whether a medication is recognized as a Brand or Generic sourced drug, identification of clinically aligned medications via therapeutic category, identification of clinically aligned medications via diagnosis code (when appropriate), identification of conversion factors that enables the software to identify dose adjusted Alternative Medications, Quantities and Days' Supply, identification of cost information that enables the software to calculate an Estimated Cost for the Chosen Medication and each Alternative Medication, and identification of a Representative NDC, either Brand or Generic, for each Alternative Medication category.

Payer Preferences Database may be the prescription alternative identification and management data repository used to store Payer formulary content. Payer Preferences Database may identify if a medication is covered or not covered and the Payer's relative preference for one medication over another medication within a therapeutic category. Payer Preferences Database may be used by the Configurable Alternatives Engine to align identified Alternative Medications with the Patient's pharmacy benefit formulary by ranking the medications. Payer Preferences Database may be an alternative to ranking Alternative Medications via Estimated Cost and may be used with a Payer Formulary or Default Formulary. Payer Preferences Database may be delivered to the CAE from participating PBMs" or directly from contracted Payers. The receipt and processing of Payer Preferences Database may be an automated process.

Provider Preferences Database may be the Prescription alternative identification and management data repository used by the Configurable Alternatives Engine to identify a Prescriber or Prescriber Group's medication preferences, if any and applicable. Prescription alternative identification and management supports may have three Provider Preferences Database scenarios: (i.) Passes an indicator to Transaction Processing Services when the Chosen Medication is a Prescriber Group Preferred Medication, (ii.) Passes an indicator to the Transaction Processing Services when an Alternative Medication is a Prescriber Group Preferred Medication, or (iii.) Replaces or prioritizes an identified Alternative Medication with a Prescriber Group Preferred Medication. The Payer may approve the preferred medications. The Payer or the Prescriber Group may identify the preferred medications.

Configurable Alternatives Engine may be the Alternative Therapy Messaging component that: receives an Alternative Therapy Request with Chosen Medication, Quantity, and Days' Supply data and pharmacy benefit information (when Patient has pharmacy benefit insurance) and optionally an assigned diagnosis; intersects the Chosen Medication, Quantity, and Days' Supply information and business rules to the Therapeutic Equivalency Database; intersects the identified Alternative Medications and the Patient's pharmacy benefit information (i.e. BIN Number, Processor Control Number, Group ID, and Cardholder ID) with the corresponding Payer Preferences Database to rank the Alternative Medications; and passes a Cost Transparency Response with up to three selected Alternative Medications to the Cost Transparency Processing component. Configurable Alternatives Engine may intersect the data and applies the rules that identify the Alternative Medications. The Cost Transparency Response data may be used to format and deliver PBM Request transactions to the Patient's Pharmacy Benefit Manager or a Drug Savings Card processor.

Figure 3A:
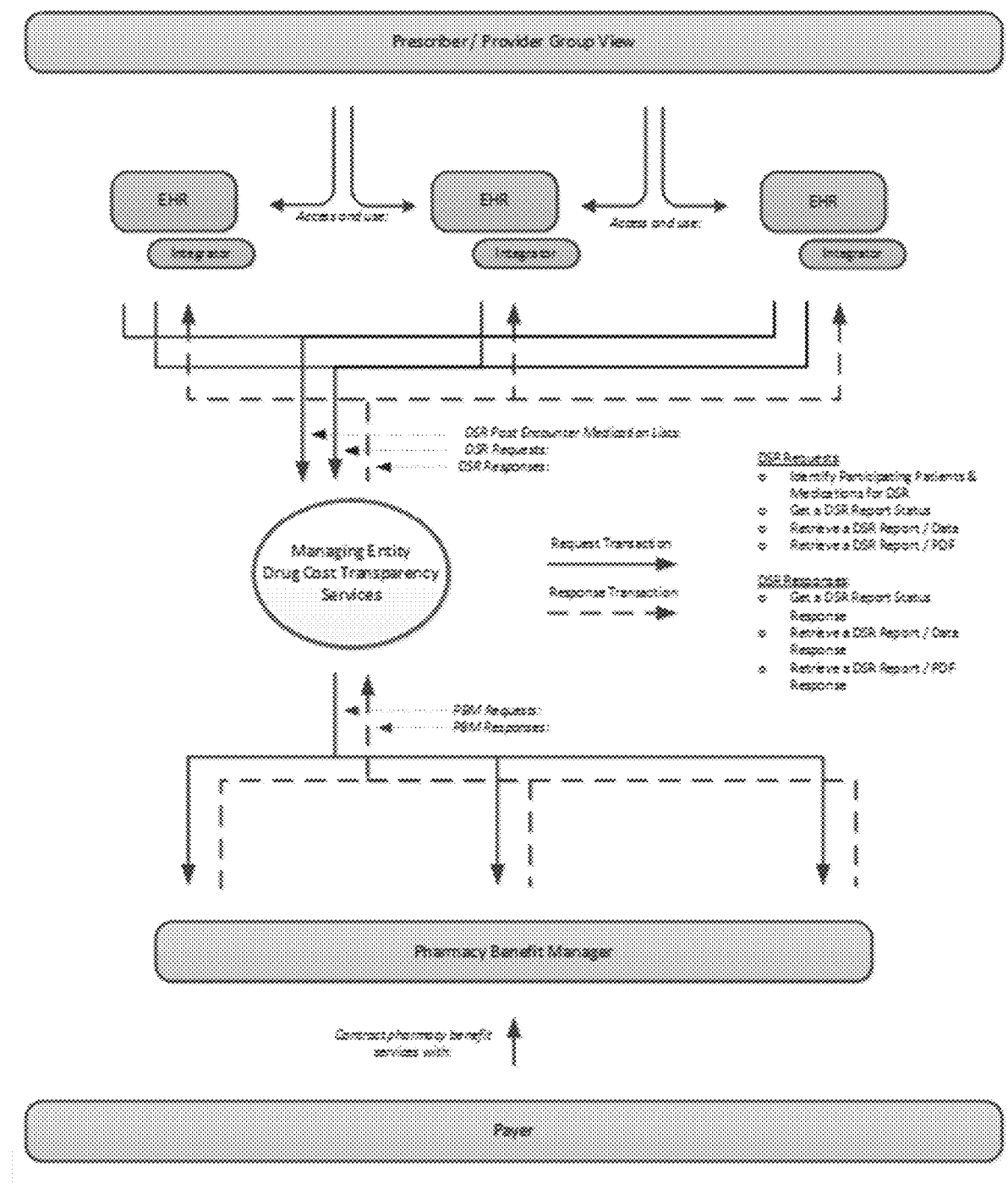
FIG. 3A is an example of a workflow showing relationships between a CAE (that may perform the methods and/or include the apparatuses described herein), the Prescriber, the EHR and the PBM.
Figure 3B:
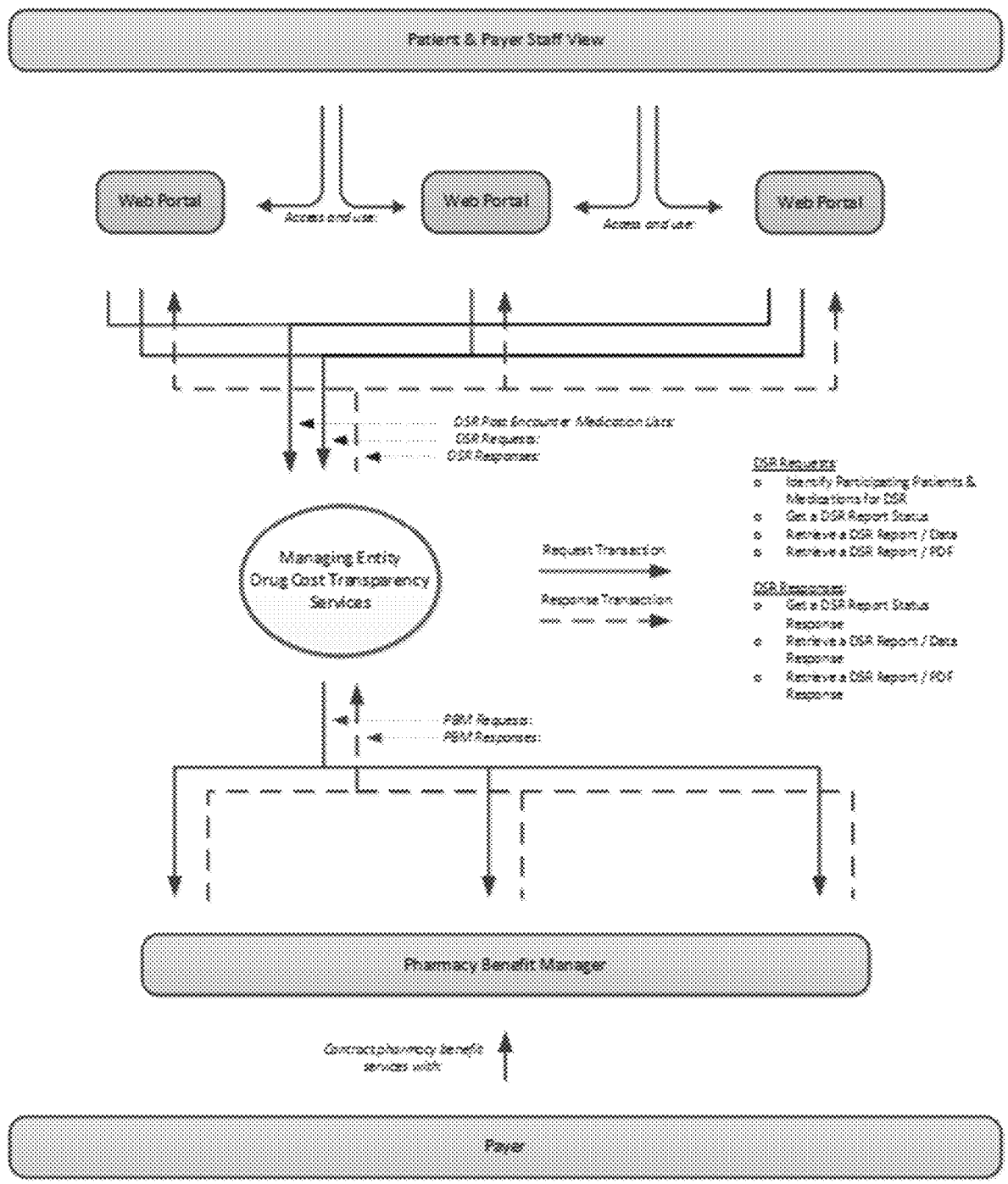
FIG. 3B is an example of a workflow showing relationships between a CAE (that may perform the methods and/or include the apparatuses described herein), the Payer or patient and the PBM.

FIGS. 3A-3B illustrate one examples of workflows showing exemplary relationships between a CAE (that may perform the methods and/or include the apparatuses described herein), the Prescriber, Payer, patient and EHR, and PBM.

For example, a CAE may be configured to generate a report (e.g., DSR) for a patient, Prescriber and/or Payer. The participating Patients and preexisting Medications may first be identified, and a trigger event may trigger processing of a report. Prescription benefit information may be included. A report request (in some variations indicating a medical benefit ID). The DSR (aka Alternatives Analysis Report or "AAA report") may be generated, and in some variations a DSR status report may be generated. As used herein AAA may refer to the drug saving reporting ("automated alternative medicines analysis"). The DSR ("DSR") may be stored, retrieved, and/or delivered. For example, a Post Encounter Medication List may be delivered to the CAE. In some variations an Alternative Medication Selection may be identified to CAE. The EHR may be allowed to bill for the DSR review by the Prescriber. The patient may be allowed to redeem or use any DSR rewards (e.g., incentive credits) to pay for some or all of their medications.

In some variations the report may be customized for a Payer. For example, the fields displayed, as well as the use/non-use of incentive credits/rewards may be selected by the Payer. The Configurable Alternatives Engine may be used to identify one or more chronic care medications (e.g., via a Chronic Care Medications database), and/or to maintain the Payer Identifier database, and/or identify participating Payers to an EHR/EHR Integrator. In some variations, the DSR Engine may create one or more DSR Activity Reports for a Payer. The DSR Engine may, e.g., deliver DSR Activity Reports to a Payer, Patient and/or Prescriber. The Managing Entity may create DSR Activity Reports for a Healthcare System. In some variations, the Managing Entity may deliver a DSR Activity Reports to a Healthcare System, and/or permit a Prescriber to review a DSR report.

EXAMPLES

Figure 4:
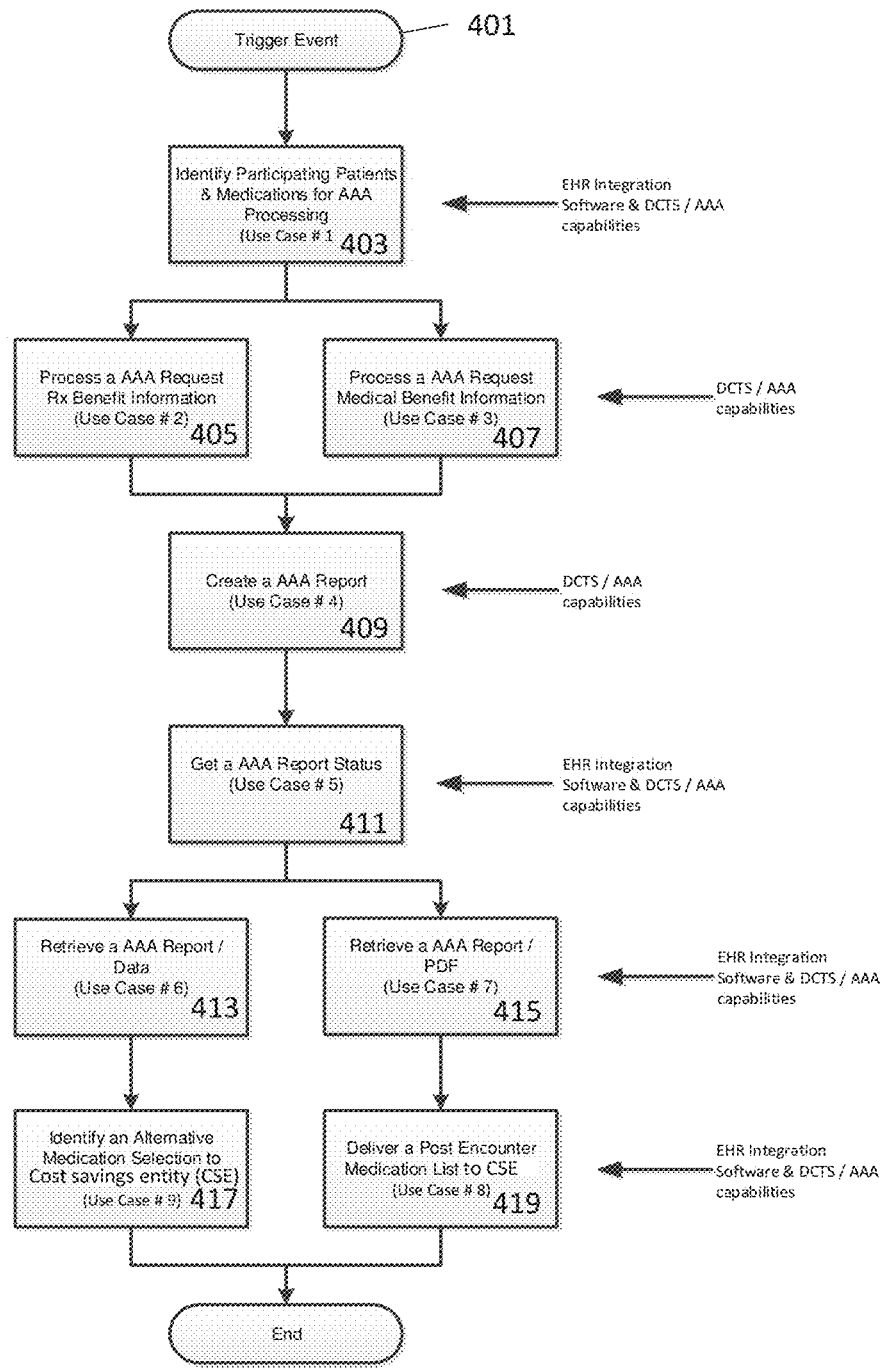
FIG. 4 is an example of a drug cost transparency services, which may be offered by, e.g., a CAE, showing nine use-case examples.

FIG. 4 illustrates an example of a drug cost transparency services, which may be offered by, e.g., a CAE. In FIG. 4, the Trigger event 401 leads to the system (e.g., a DSR system) to identify Participating Patients & Existing Medications for automated alternative analysis (AAA) 403. In this step, the EHR Integration Software may determine it is time to identify Patients with an upcoming appointment and initiates a request to the Electronic Health Record (EHR) for this information, as well as how the EHR provides this information, how the EHR Integration Software requests the identification of the Patient's demographic, preferred pharmacy and pharmacy benefit information, how the EHR provides this information, how the EHR Integration Software receives the information and identifies a Patient or subset of Patients corresponding to a Participating Payer (i.e. Participating Patients), and submits a request to identify the medication list that corresponds to the Participating Patients, how the EHR provides this information and how the EHR Integration Software delivers this information to the DSR Engine as a DSR Report Request, either per Patient per DSR request or multi-Patients per DSR request. This method may identify processes that occur at the EHR/EHR Integrator. Use this technique processing steps may be combined. DSR Engine will create and maintain a common vocabulary of Payer Identifiers. DSR Engine does not have to deliver an acknowledgement/response to the EHR Integration Software.

In FIG. 4 the Managing Entity is shown contracted with an EHR for DSR Services. Authentication, authorization, and handshake rules may be established and used for EHR Integration Software and DSR Engine DSR communications. Participating EHR may/may not be contracted for DCTS/New Rx's.

In any of these methods and apparatuses, the patient's EHR Integration Software may support one or more of the following scenarios: Upcoming Appoint—Automatically triggers a DSR Request, a Refill Reminder that automatically triggers a DSR Request; Prescriber Initiated—the end-user may triggers a DSR Request. This apparatus and method may also include EHR Integration Software that can identify the DSR Request type, such as an upcoming Appointment, a Refill Request, a Prescriber Initiated, etc.

Some variations of the EHR Integration Software (cost control can identify the medical benefit plan/Payer (e.g. Florida Blue), or pharmacy benefit manager (e.g. PBM2) of the Patient and can therefore deliver to the DSR Engine all, some, of the following data: Medical Benefit—Payer Name/ID; Medication Benefit—Member ID; Pharmacy Benefit—BIN Number, Pharmacy Benefit—Processor Control Number, Pharmacy Benefit—Group ID, and Pharmacy Benefit—Cardholder ID. In some variations, the EHR Integration Software can identify information that describes the Patient by: Patient First Name, Patient Last Name, Patient Date of Birth, Patient Gender Code, EHR Patient ID, and/or Patient's Preferred Pharmacy ID (optional). The Patient's Preferred Pharmacy identification is desired, but not a mandatory. DCTS will assign a default pharmacy identifier if the Patient's preferred pharmacy is not delivered in the DSR Request.

EHR Integration Software may access, and may therefore deliver to DSR Engine, the following EHR specific data: Institution ID, EHR Patient ID, DSR Request Type (Upcoming Appointment, Refill Reminder, or Prescriber Initiated), EHR Integration Software can capture information that describes the Prescriber requesting the DSR: Prescriber ID (NPI); Prescriber Last Name; Prescriber Phone Number; EHR Integration Software can identify information that describes the Patient's medications: Medication ID (RxNorm or Representative NDC), Quantity (optional), such as Days' Supply (optional but preferred), Prescriber Last Name (optional but preferred), Prescriber Phone Number (optional but preferred); Quantity and Days' Supply data are desired, but not mandatory, fields. DCTS will assign a default Quantity and Days' Supply if the data is not delivered in the DSR Request.

If the DSR Request is for an upcoming Patient visit, the DSR Request may be delivered at least one business day preceding the Patient's appointment, and the DSR Engine does not have to acknowledge receipt of a DSR Request.

Any of these methods and apparatuses described herein may be subject to one or more pre-conditions. Pre-Conditions (i.e. dependencies that are internal to the solution) supporting this Use Case include: Participating Payer(s) (e.g. Florida Blue) identified to the EHR Integration Software; DSR Request transaction format identified to the solution; and/or Institution ID pre-assigned for the Healthcare System or Prescriber Group delivering the DSR Request In practice, the EHR Integration Software may be configured to: determine it is time to identify Patients with an upcoming appointment, communicate a request to the EHR to identify Patients with an upcoming appointment. An Electronic Health Record may include: receiving the request to identify Patients with an upcoming appointment (e.g. next business day); communicating a list of Patients with an upcoming appointment to the EHR Integration software. The EHR Integration software may: receives a response that identifies Patients with an upcoming appointment, and/or communicate a request to the EHR to identify each Patient's demographic, preferred pharmacy, and insurance information.

The patient's electronic health record (EHR) may generally: receive the request to identify the Patient's demographic, preferred pharmacy, and insurance benefit information; communicate the Patient's demographic, preferred pharmacy, and insurance benefit information to the EHR Integration Software. The EHR Integration Software may: receive the Patient's demographic, preferred pharmacy and insurance benefit information, determines if the Patient's insurance benefit information corresponds to a list of Participating Payers' (if "Participating Payer"—e.g., primary path, continue processing, and if "Not a Participating Payer"—discard Patient record). The EHR may communicate a request to identify the Patient's (Participating Payer) medication list.

The EHR may: receives the request to identify the Patient's medication list, and/or capture the DSR Request Type, such as: Upcoming Appointment, Refill Request, or Prescriber Initiated.

Captures Patient attribute data may include: EHR Patient ID, Participating Payer ID/Name, Patient First Name, patient Last Name, Patient Date of Birth, etc. Additional data may include: patient Gender Code, medical Benefit/Member ID, Rx Benefit/BIN Number, Rx Benefit/Processor Control Number, Rx Benefit/Group ID (Varies by Payer); Rx Benefit/Cardholder ID, patient's Preferred Pharmacy ID, etc. Other optional features may include capturing initiating institution and initiating Prescriber information, institution ID, Prescriber ID: [NPI]; Prescriber Last Name, Prescriber Phone Number: captures the current medication history for each Participating Patient; date of Service, Prescriber Last Name, medication ID; RxNorm or representative NDC: quantity (Optional) Optional/Repeating; days' Supply, etc.

The system may format a DSR Request as: (i.) a Single Patient/Multiple Medications, e.g., for each Participating Patient that includes their Medication History, r (ii.) Multiple Patients/Multiple Medications—for all Participating Patients and their corresponding medications. The DSR Request may be delivered to DSR Engine.

For example the DSR Engine may: Receive the DSR Request; Capture the DSR Request data for DSR processing. Conditions for this may include, the EHR may identify Patients with an upcoming appointment; identified demographic, preferred pharmacy, and benefit information for Patients with an upcoming appointment; identified medication list information for Participating Patients. The EHR Integration Software may have: communicated a request to identify Patients with an upcoming appointment; captured the EHR's Response to the preceding request; communicated a request to identify the demographic, preferred pharmacy, and insurance benefit of the Patients with an upcoming appointment, captured the EHR's Response to the preceding request; identified the subset of Patient's corresponding a Participating Payer; communicated a request to identify the medication list for each Participating Patient; captured the EHR's Response to the preceding request: formatted a DSR Request from the captured information (e.g., single Patient/Multiple Medications, multiple Patients/Multiple Medications, etc.). The EHR Integration software may deliver a DSR Request(s) to the DSR Engine. The DSR Engine (e.g., DCTS/DSR) may receive a DSR Request(s) and process the request. Processing a DSR Request (with Rx Benefit Information Included) was a second example in FIG. 4 ('use case 2'). In this example, the DSR Engine may determine a DSR Request is ready for processing, determine the DSR Request includes the Patient's pharmacy benefit information, identify the pharmacy claims processor corresponding to the Patient's pharmacy benefit information, interface with the Configurable Alternatives Engine to identify up to 3 dose equivalent and formulary aligned Alternative Medications, format a PBM Request for each Existing Medication and their corresponding Alternative Medications, and delivers a PBM Request for each medication to the PBM, how the pharmacy claims processor; receives the PBM Request, adjudicates the PBM Request, and deliver a PBM Response to Configurable Alternatives Engine, and how Configurable Alternatives Engine; captures the PBM Response data. This example, also supports multiple Payer Configurations: Chronic Care or All (Exclude Acute Care Medications), Non-Preferred or All (Exclude Preferred Medications), not the Lowest Tier or all (Exclude Lowest Tier Medications), and DSR Creation Frequency.

The second example (second use case) 405 is shown in FIG. 4. In this example, the DCTS/DSR validates submitted BIN Number & Processor Control Number combination before delivering a PBM Request. The DCTS/DSR validates "minimum necessary" data requirements before formatting a PBM Request. The DCTS/DSR uses the same DCTS transaction formatting and delivery rules as the transaction formatting and delivery rules as the core DCTS/New Rx's solution. The DCTS/DSR uses the same CAE processing rules as the DCTS/New Rx's solution, including: identification of Alternative Medications, identification of Preferred Medications, and identification of Excluded Medications. The DCTS/DSR delivers PBM Request transactions to the Pharmacy Claims Processor in sequential order. DCTS/DSR delivers PBM Request transactions in "first in/first out" order. There is no medication or therapeutic preference for sequencing. The First Medication is the initial medication presented to the DCTS solution. No attempt is made to sequence or prioritize the medications. The Next Medication is any additional, Patient-specific medications presented to the DCTS solution that follows a First Medication. DSR processing halts if the First Medication received a Rejected PBM Response and the reject is eligibility reject. A Medication is not included on the DSR if an Alternative Medication does not exist.

Pre-Conditions (i.e. dependencies that are internal to the solution) supporting this Use Case may include: PBM Request/Minimally Necessary data configured/identified, Eligibility reject reason(s) configured/identified, "07" (M/I Cardholder ID, "65" (Patient is Not Covered), "68" (Filled After Coverage Expired), and "69" (Filled After Coverage Terminated), participating Payer configured to exclude Acute Care Medications, Participating Payer configured to exclude Preferred Medications, Participating Payer configured to exclude Lowest Tier Medications, Participating Payer configured to limit reports to 1 report per member per X days, PBM Request/Transaction Format configured/identified, and CAE/Payer Configurations configured/identified In an exemplary Process Flow: DSR Engine DCTS/DSR: determines if there is a DSR Request ready for processing, "DSR Request"—primary path, continues processing, "No DSR Request"—alternate path, processing halts (determines if the DSR Request includes the Patient's pharmacy benefit information, e.g., BIN Number, Processor Control Number, & Cardholder ID: "Rx Benefit Information"—primary path, continue processing at the next step, or "No Rx Benefit Information/Member ID"—alternate path and alternate use case), determines if the Patient/member received a DSR within the Payer configured frequency limit (e.g. 1 report per member per 365 days): identifies the Payer and Patient/Member IDs, determines if the Patient/Member ID previously received a DSR by matching the Payer and Patient/Member IDs to a file of Payer and Patient/Member ID's that previously received a DSR. If "DSR Not Previously Delivered"—primary path, continues processing at the next step, or if "DSR Previously Delivered"—alternate path, determines if the number of days since the last report was delivered is greater than the Participating Payer minimum number of interval days between report creations; if "Does not Exceed Minimum Interval Days", halts processing of the DSR, or if "Exceeds Minimum Interval Days", continues processing at the next step. Determines if the DSR Request includes the minimally necessary data to format a PBM Request to the pharmacy claims processor responsible for managing the Patient pharmacy benefit: "Meets Minimally Necessary Data"—primary path, continue processing; "Does not meet Minimally Necessary Data"—alternate path, processing halts. Determines, for the Participating Payer, if the DSR includes Acute Care Medications: "Exclude Acute Care Medications", a primary path, continue processing at the next step; "Include Acute Care Medications", an alternate path, skip the next processing step. Identifies, for the First/Next Medication, if the medication (i.e. Existing Medication) is an Acute Care Medication: "Not an Acute Care"—primary path, processing continues at the next step, or "Acute Care Medication"—alternate path: Exclude Acute Care Medication from DSR, and Continue processing as above. Determines, for the Participating Payer, if the DSR includes Preferred Medications; "Exclude Preferred Medications"—primary path, processing continues at the next step, or "Include Preferred Medications"—alternate path, processing skips the next processing step, Identifies, for the First/Next Medication, if the medication (i.e. Existing Medication) is a Preferred Medication; "Not a Preferred Medication"—primary path, processing continues at the next processing step "Preferred Medication"—alternate path: Exclude Preferred Medication from DSR, and Continue processing as above. Determines, for the Participating Payer, if the DSR includes Lowest Tier Medications: "Exclude Lowest Tier Medications"—primary path, processing continues at the next step, or "Include Lowest Tier Medications"—alternate path, processing skips the next processing step, identifies, for the First/Next Medication, if the medication (i.e. Existing Medication) is a Lowest Tier Medication: "Not a Lowest Tier Medication"—primary path, continue processing at the next step; "Lowest Tier Medication"—alternate path: Exclude Lowest Tier Medication from DSR, Continue processing at the next step. Determines if there is a "Next Medication" to process, "Next Medication"—primary path, continues processing as above:

"No Next Medication"—alternate path, continues processing at the next step, interfaces with the Configurable Alternatives Engine to identify up to three dose and formulary aligned alternative medications, formats a PBM Request using the Remaining Medications and configuration parameters provided by the PBM: Chosen Medication, and up to 3 Alternative Medications. Delivers a PBM Request for the First/Next Medication, along with up to 3 Alternative Medications, to the Pharmacy Claims Processor. The Pharmacy Claims Processor: Receives the PBM Request, Adjudicates the PBM Request, and Communicates a PBM Response The Configurable Alternatives Engine DCTS/DSR: receives a PBM Response, determines if the PBM Response is a First Medication, "First Medication"—continue processing at the next step, or "Next Medication"—skips the next two processing steps. Determines, for a "First Medication", if the PBM Response was an Approved PBM Response or a Rejected PBM Response: "Rejected PBM Response"—continue processing at the next step, or "Approved PBM Response"—skips the next processing step. Determines, for a First Medication that resulted in a Rejected PBM Response, if the denial is an eligibility denial: "Not an Eligibility Denial"—primary path, continue processing; "Eligibility Denial"—alternate path: Captures the Rejected PBM Response details, and Halts further processing for this Patient, Captures the PBM Response data, and Determines if there is a "Next Medication" for the Patient identified to the DSR Request: "Next Medication"—continue processing by initiating "Next Medication" processing at the Chronic Care/Acute Care determination step, "No Next Medication"—continue processing at the next step. Determines if the minimum requirements for delivering a DSR have been met (i.e. At least one Alternative Medication opportunity with/without a total Savings calculation.): "Minimum Requirements Met"—takes the following steps: Captures the Payer ID, Member/Patient ID and the Date the DSR was created in a Report Created File; Continue processing at the next step: "Minimum Requirements Not Met"—continue processing at the next step. Processing halts for this Member/Patient.

The DSR Engine may have: determined a DSR Request was ready for processing, determined the DSR Request included pharmacy benefit information (Use Case #2 specific), determined the DSR Request included minimally necessary data to format a PBM Request, determined the Participating Payer is configured to exclude creation of a DSR if the Member/Patient received a DSR and a minimum number of interval days have not passed. determined the combination of Participating Payer and Member/Patient ID had not received a DSR within the Payer configured minimal interval period, determined the Participating Payer is configured to exclude Acute Care Medications from the DSR, determined, for each Existing Medication, if the medication is classified as an Acute Care or Chronic Care Medication, excluded/filtered any Existing Medications identified as Acute Care from the DSR, determined the Participating Payer is configured to exclude Preferred Medications from the DSR, determined, for each Existing Medication, if the medication is classified is a Preferred Medication, excluded/filtered any Existing Medications identified as "Preferred Medications" from the DSR, determined the Participating Payer is configured to exclude Existing Medications assigned to the lowest tier within the formulary, excluded/filtered any Existing Medications assigned to the lowest tier within a therapeutic category, identified, for each remaining Existing Medication, up to 3 dose equivalent and formulary aligned Alternative Medications, formatted and delivered a PBM Request to the Patient's pharmacy claims processor for each Chronic Care Medication identified to the DSR Request, received a PBM Response for each Chronic Care Medication and any Alternative Medications, captured the PBM Response data for each Chronic Care Medication and any Alternative Medications for the DSR creation, determined the minimum requirements for delivering a DSR have been met, and added Payer, Member/Patient ID, and Date DSR is created to a file of created reports.

The Pharmacy Claims Processor may have: received at least one PBM Request, adjudicated each PBM Request, and communicated a PBM Response for each medication.

Another example (use case #3) describes how DSR Engine determines a DSR Request is ready for processing, determines the DSR Request includes the Patient's Medical Benefit Identifier, identifies the Patient's pharmacy benefit information from the Medical Benefit Identifier, identifies the pharmacy claims processor corresponding to the Patient's pharmacy benefit information, interfaces with the Configurable Alternatives Engine to identify up to 3 dose equivalent and formulary aligned Alternative Medications, formats a PBM Request for each Existing Medication and their corresponding Alternative Medications, and delivers a PBM Request for each medication to the PBM, how the pharmacy claims processor; receives the PBM Request, adjudicates the PBM Request, and delivers a PBM Response to Configurable Alternatives Engine, and how Configurable Alternatives Engine captures the PBM Response data.

Use Case #3 407 (see FIG. 4, above) substantially overlaps with Use Case #2 but interfaces with a Member Eligibility file to identify the Patient's pharmacy benefit information from the submitted Medical Benefit Identifier. Assumptions (i.e. dependencies that are external to the solution) supporting this Use Case include the same assumptions as use Case #2, above. Pre-Conditions (i.e. dependencies that are internal to the solution) supporting this Use Case include the same Pre-Conditions as Use Case #2

The DSR Engine determines if there is a DSR Request ready for processing: "DSR Request"—primary path, continues processing "No DSR Request"—alternate path, processing halts. It also determines if the DSR Request includes the Patient's pharmacy benefit information (BIN Number, Processor Control Number, & Cardholder ID): "No Rx Benefit Information"—primary path, continue processing at the next step, or "Rx Benefit Information/Member ID"—alternate path and alternate use case (UC #2). It also identifies the Patient's pharmacy benefit information from the submitted Medical Benefit Identifier. It also determines if there is minimally necessary data to deliver a PBM Request to the pharmacy claims processor responsible for managing the Patient's pharmacy benefit: "Meets Minimally Necessary"—primary path, continue processing. It also determines if the Patient/member received a DSR within the Payer configured frequency limit (e.g. 1 report per member per 365 days): identifies the Payer and Patient/Member IDs; determines if the Patient/Member ID previously received a DSR by matching the Payer and Patient/Member IDs to a file of Payer and Patient/Member ID's that previously received a DSR: if "DSR Not Previously Delivered"—primary path, continues processing at the next step, or if "DSR Previously Received"—alternate path, determines if the number of days since the last report was delivered is greater than the Participating Payer minimum number of interval days between report creations, if "Does not Exceed Minimum Interval Days", halts processing of the DSR, or if "Exceeds Minimum Interval Days", continues processing at the next step. It also determines, for the Participating Payer, if the DSR includes Acute Care Medications: "Exclude Acute Care Medications"—primary path, continue processing at the next step; "Include Acute Care Medications"—alternate path, skip the next processing step. It also identifies, for the First/Next Medication, if the medication (i.e. Existing Medication) is an Acute Care Medication: "Not an Acute Care"—primary path, processing continues at the next step, or; "Acute Care Medication"—alternate path: exclude Acute Care Medication from DSR, and continue processing at a step above. It also determines, for the Participating Payer, if the DSR includes Preferred Medications: "Exclude Preferred Medications"—primary path, processing continues at the next step, or "Include Preferred Medications"—alternate path, processing skips the next processing step. It also identifies, for the First/Next Medication, if the medication (i.e. Existing Medication) is a Preferred Medication: "Not a Preferred Medication"—primary path, processing continues at the next processing step; "Preferred Medication"—alternate path: Exclude Preferred Medication from DSR, and Continue processing at a step above. It also determines, for the Participating Payer, if the DSR includes Lowest Tier Medications: "Exclude Lowest Tier Medications"—primary path, processing continues at the next step, or "Include Lowest Tier Medications"—alternate path, processing skips the next processing step. It also identifies, for the First/Next Medication, if the medication (i.e. Existing Medication) is a Lowest Tier Medication: "Not a Lowest Tier Medication"—primary path, continue processing at the next step: "Lowest Tier Medication"—alternate path, Exclude Lowest Tier Medication from DSR, Continue processing at the next step. It also determines if there is a "Next Medication" to process: "Next Medication"—primary path, continues processing at a step above; "No Next Medication"—alternate path, continues processing at the next step. It also interfaces with the Configurable Alternatives Engine to identify up to three dose and formulary aligned alternative medications. It also formats a PBM Request according to the specifications provided by the PBM: Chosen Medication, and up to 3 Alternative Medications; delivers a PBM Request for the First/Next Medication, along with up to 3 Alternative Medications, to the Pharmacy Claims Processor: Pharmacy Claims Processor: Receives the PBM Request, Adjudicates the PBM Request, and Communicates a PBM Response.

The Configurable Alternatives Engine DCTS/DSR also: Receives a PBM Response, Determines if the PBM Response is for the First Medication: "First Medication"—continue processing at the next step, or "Next Medication"—skips the next two processing steps. It also determines, for a "First Medication", if the PBM Response was an Approved PBM Response or a Rejected PBM Response: "Rejected PBM Response"—continue processing at the next step, or "Approved PBM Response"—skips the next processing step. It also determines, for a First Medication that resulted in a Rejected PBM Response, if the denial is an eligibility denial: "Not an Eligibility Denial"—primary path, continue processing; "Eligibility Denial"—alternate path: captures the Rejected PBM Response details, and halts further processing for this Patient. It also captures the PBM Response data, and determines if there is a "Next Medication" for the Patient identified to the DSR Request: "Next Medication"—continue processing by initiating "Next Medication" processing at the Chronic Care/Acute Care determination step; "No Next Medication"—continue processing at the next step. It also determines if the minimum requirements for delivering a DSR have been met (i.e. At least one Alternative Medication opportunity with/without a total Savings calculation.); "Minimum Requirements Met", takes the following steps: Captures the Payer ID, Member/Patient ID and the Date the DSR was created in a Report Created File, Continue processing at the next step, "Minimum Requirements Not Met"—continue processing at the next step. Processing halts for this Member/Patient.

Post-processing, the DSR Engine DCTS/DSR: determined a DSR Request was ready for processing, determined the DSR Request contained medical benefit rather than pharmacy benefit information, identified the Patient's pharmacy benefit information from the submitted Medical Benefit Identifier. It also determined the DSR Request included minimally necessary data to format a PBM Request: determined the Participating Payer is configured to exclude creation of a DSR if the Member/Patient received a DSR and a minimum number of interval days have not passed; determined the combination of Participating Payer and Member/Patient ID had not received a DSR within the Payer configured minimal interval period, determined the Participating Payer is configured to exclude Acute Care Medications from the DSR, determined, for each Existing Medication, if the medication is classified as an Acute Care or Chronic Care Medication: excluded/filtered any Existing Medications identified as Acute Care from the DSR. It also determined the Participating Payer is configured to exclude Preferred Medications from the DSR, determined, for each Existing Medication, if the medication is classified is a Preferred Medication, excluded/filtered any Existing Medications identified as "Preferred Medications" from the DSR, determined the Participating Payer is configured to exclude Existing Medications assigned to the lowest tier within the formulary, excluded/filtered any Existing Medications assigned to the lowest tier within a therapeutic category, identified, for each remaining Existing Medication, up to 3 dose equivalent and formulary aligned Alternative Medications, formatted and delivered a PBM Request to the Patient's pharmacy claims processor for each Chronic Care Medication identified to the DSR Request, received a PBM Response for each Chronic Care Medication and any Alternative Medications, captured the PBM Response data for each Chronic Care Medication and any Alternative Medications for the DSR creation and determined the minimum requirements for delivering a DSR have been met, and added Payer, Member/Patient ID, and Date DSR is created to a file of created reports: Pharmacy Claims Processor. It also received at least one PBM Request, adjudicated each PBM Request, and communicated a PBM Response for each medication.

Example 4 (use Case #4) 409 (in FIG. 4) describes how the DSR Engine determines a DSR is ready to be created, identifies the PBM Request and Response data for the Existing Medications and the corresponding Alternative Medications, calculates an Annual Patient Savings and an Annual Total Savings for each Alternative Medication, calculates an Estimated Patient Reward for each Alternative Medication, calculates an Aggregated Annual Patient Savings and Aggregated Annual Total Savings, determines if either the Aggregated Annual Patient Savings or Aggregated Annual Total Savings meet a minimum Payer threshold, and determines how the EHR Integration Software originating the DSR Request wants to receive the DSR, and creates the DSR.

Use Case #4 identifies new capabilities that reside at DSR Engine. The foundation version of the DSR will not present Alternate Fulfillment savings. The "Estimated Patient Reward" calculation is a foundation capability. However, the "Estimated Patient Reward" is not defined to the foundation version of the DSR. Use Case #4 supports multiple Payer Configurations: Estimated Patient Reward, Minimum Aggregated Annual Patient Savings Threshold (Default value of $250), and Minimum Aggregated Annual Total Savings Threshold (Default value of $250)

Assumptions (i.e. dependencies that are external to the solution) supporting this Use Case may include and of the following. The DSR identifies Existing Medications receiving an Approved PBM Response. The DSR does not include Existing Medications that receive a Rejected PBM Response. The DSR identifies Existing Medications with an Alternative Medication. The DSR does not include Existing Medications without an Alternative Medication. The DSR identifies Existing Medications: with Annual Patient Savings and without Annual Patient Savings; with Annual Total Savings and without Annual Total Savings. The calculation of an Annual Patient Savings varies by PBM (See below in each of Examples "C", "D", "E", and "F"): PBM1, PBM2. The calculation of an "Estimated Patient Reward" varies by Payer and potentially by PBM (Pharmacy Benefit Manager). The Minimum Aggregated Annual Patient Savings and Minimum Aggregated Annual Total Savings use Participating Payer defined configuration parameters. The DSR may be unable to calculate an Annual Patient Savings calculation if a deductible is involved for certain PBMs: PBM1a.

The pre-Conditions (i.e. dependencies that are internal to the solution) supporting this use Case may include: annual Patient Savings calculations per PBM defined to the solution, annual total Savings calculations per PBM defined to the solution, identification of whether the PBM communicates Comprehensive Deductible Information configured to the solution, identification of whether the PBM communicates financial information on rejects configured to the solution; estimated Patient Reward calculations per PBM defined to the solution; identification of the following thresholds are defined to the solution: minimum Aggregated Annual Total Savings Threshold, and minimum Aggregated Annual Total Savings Threshold.

The DSR Engine typically determines if there is a DSR to create: "DSR"—primary path, continues processing, or "No DSR"—alternate path, processing halts. It also captures the date the report is created. It also captures information that describes the Patient/member: Patient/Member First Name, Patient/Member Last Name. It also identifies the PBM Response data for the First/Next Medication. It also determines if the First/Next Medication received an Approved CT Response: if "Approved CT Response"—primary path, continues processing at the Approved CT Response step, or if "Rejected CT Response"—alternate path, continues processing: removes First/Next Existing Medication from inclusion in the DSR, and continues processing at a next step.

The approved CT Response (for an Existing Medication) determines if the DCTS solution identified one or more Alternative Medications corresponding to the Approved CT Response: if "Alternative Medications"—takes the following steps: identifies the following information for the First/Next Existing Medication (i.e. First/Next Existing Medication is complete): Medication Name & Strength, Medication Quantity, and Medication Dosage Form, and continues processing at the next step, or: If "No Alternative Medications"—Determines if there is a Next Existing Medication and initiates the process, "Next Existing Medication"—continues processing at another step: "No Next Existing Medication"—processing halts. It also determines, for each Alternative Medication, if the Alternative Medication received an Approved PBM Response or a Rejected PBM Response. If "Approved PBM Response"—continues processing: identifies the following information for the First/Next Existing Medication: medication Name & Strength, Medication Quantity, and Medication Dosage Form: skips the next processing step: if "Rejected PBM Response"—continues processing, identifies the primary reject reason, and continues processing at another step. It also determines if the Existing Medication includes a Patient financial responsibility attributable to a deductible: if "No Deductible"—primary path, continue processing at the next step, or, if "Deductible"—alternate path, take the following steps: capture indicator that an Annual Patient Savings is not available due to a deductible, & processing continues at the Calculate total Annual Savings Step. It also determines if the Existing Medication includes coverage gap dollars: If "No Coverage Gap"—primary path, continue processing at the next step, or, If "Coverage Gap"—alternate path, take the following steps: capture indicator that an Annual Patient Savings is not available due to a deductible, and processing continues at the Calculate total Annual Savings Step. It also calculates the following Annual Savings: annual Patient Savings, and Annual Total Savings. It also calculates an "Estimated Patient Reward" for each Current Medication (see, below, Example G). It also determines if there is a Next Existing Medication to process: "Next Existing Medication"—continues processing at another step; "No Next Existing Medication"—continues processing at "Calculate Annual Savings".

It may calculate Annual Savings (Patient & total) by: identifies the First/Next Existing Medication/Alternative Medication pair, calculates an Annual Patient Savings (see below for PBM2 calculations, and see Appendix D for PBM1 calculations); processing continues at the next step. It also calculates an Annual Total Savings (see below for PBM2 calculations, see Appendix E for PBM1 calculations) and processing continues at the next step. It also determines if there is a Next Existing Medication/Alternative Medication Pair: "Next Existing Medication/Alternative Medication Pair"—processing continues at another step; "No Next Existing Medication/Alternative Medication Pair"—processing continues at the next step.

The approved CT Response also calculates "Aggregated Annual Patient Savings": identifies the First/Next Existing Medication, identifies the Alternative Medications for each Existing Medication, identifies the Annual Patient Savings for each Alternative Medication, identifies the Alternative Medication with the greatest Annual Patient Savings, determines if there is Next Existing Medication: if "Next Existing Medication"—continues processing at another step; and if "No Next Existing Medication"—continues processing at the next step; adds the Annual Patient Savings for each Existing Medication/Alternative Medication to identify a "Aggregated Annual Patient Savings"; continues processing a "Calculates Aggregated Annual Total Savings".

It also calculates "Aggregated total Patient Savings": identifies the First/Next Existing Medication; identifies the Alternative Medications; identifies the Annual Total Savings for each Alternative Medication; identifies the Alternative Medication with the greatest Annual Total Savings; determines if there is Next Existing Medication: if "Next Existing Medication"—continues processing at another step; if "No Next Existing Medication"—continues processing at the next step. It also adds the Annual Total Savings for each Existing Medication/Alternative Medication pair to identify an "Aggregated Annual Total Savings"; and continues processing a "Calculates Minimum Savings Threshold".

It also Calculates Minimum Threshold Savings. For example, it identifies Aggregated Annual Patient Savings;

identifies Minimum Aggregated Annual Patient Savings Threshold for the Participating Payer; determines if the Aggregated Annual Patient Savings equals or exceeds the Minimum Aggregated Annual Patient Savings defined by the Participating Payer: if "Minimum Aggregated Annual Patient Savings Met" (sets minimum threshold indicator to "Yes"; continues processing at the next step) If "Minimum Aggregated Annual Patient Savings Not Met" (sets minimum threshold indicator to "No"), and continues processing at the next step. It also identifies the Aggregated Annual Total Savings, identifies the Minimum Aggregated Annual Total Savings Threshold for the Participating Payer, determines if the Aggregated Annual Total Savings equals or exceeds the Minimum Aggregated Annual Total Savings defined by the Participating Payer: if "Minimum Aggregated Annual Total Savings Met" (sets minimum threshold indicator to "Yes"; continues processing at the next step); if "Minimum Aggregated Annual Total Savings Not Met" (sets minimum threshold indicator to "No") and continues processing at the next step. It also determines if either the Minimum Aggregated Annual Patient Savings or Minimum Aggregated Annual Total Savings thresholds were met. If either threshold met, continue processing at "Identify Patient's Preferred Pharmacy Information", or if either threshold not met, discontinue DSR Processing for this Patient.

The approved CT Response may also identify Patient's Preferred Pharmacy Information. For example, it identifies the Patient's Preferred Pharmacy from the DSR Request; identifies the following information: Pharmacy Name, Pharmacy Street Address, and creates the DSR.

In the post-conditions for this example, the DSR Engine may have: determined a DSR opportunity was ready for processing, identified CT Response Data for the Existing Medications identified by the DSR Request and the corresponding Alternative Medications, identified subset of Existing Medications with an Approved PBM Response, identified corresponding Alternative Medications, identified subset of Alternative Medications with an Approved PBM Response, calculated an Annual Patient Savings for each Alternative Medication receiving an Approved PBM Response, calculated an Annual Total Savings for each Alternative Medication receiving an Approved PBM Response, calculated an "Aggregated Annual Patient Savings" for the remaining Existing/Alternative Medication pairs, calculated an "Aggregated Annual Total Savings" for the remaining Existing/Alternative Medication pairs, determined if Minimum Savings Thresholds were met, identified information that described the Patient's Preferred Pharmacy, and created a DSR. The system may get a DSR Status.

Example 5 (use case #5) 411 (FIG. 4) describes how the EHR Integration Software initiates and delivers a DSR Get DSR Status Request to DSR Engine, how DSR Engine authenticates the communication, accepts the Get DSR Status Request, identifies the Institution ID and Member ID, determines the Institution ID and Member ID match an existing DSR Request for the same Institution ID and Member ID, identifies the DSR Status, and delivers a Get DSR Status Response to the EHR Integration Software, and how the EHR Integration Software receives the response.

Use Case #5 identifies processes that occur at DSR Engine DCTS/DSR and at the EHR Integration Software. The Get DSR Status Request/Response is a synchronous communication. DSR Engine will provide time interval guidance on when the EHR Integration Software should follow-up a DSR Request with a Get DSR Status Request.

The assumptions (i.e. dependencies that are external to the solution) supporting Example 5 include: authentication, authorization, and handshake rules established for EHR Integration Software and DSR Engine DCTS/DSR communications, EHR Integration Software previously submitted a DSR Request to DSR Engine, and institution ID and Member ID on the Get DSR Status Request matches the Institution ID and Member ID on a previously submitted DSR Request.

Pre-Conditions (i.e. dependencies that are internal to the solution) supporting this Use Case include authentication processes co-implemented.

In operation, this use-case includes: EHR Integration Software, which determines it is time to see if a DSR is ready for pick-up, formats a Get DSR Status Request using agreed upon specifications, and initiates secure communications with DSR Engine DCTS/DSR. It also includes DSR Engine DCTS/DSR, which: determines if the DSR Status Request is an authorized transaction An authorized primary path may take the following actions: delivers an Authorized Request response to the EHR Integration Software, and awaits next communication; a "Not Authorized" alternate path, take the following actions: captures the transaction details, and delivers an Unauthorized Request response to the EHR Integration Software.

The EHR Integration Software receives a handshake response indicating the communication is Authentic, and delivers the Get DSR Status Request to DSR Engine DCTS/DSR.

The DSR Engine DCTS/DSR: receives the Get DSR Status Request, and determines if the DSR Status Request is properly formatted: "Properly Formatted"—primary path, continues processing at the next step, while "If Not Properly Formatted"—alternate path, take the following actions: captures the transaction details, delivers an Invalid Parameter response to the EHR Integration Software, and determines if the DSR Status Request includes minimally necessary data. The "Minimally Necessary Data" primary path continues processing at the next step, while the "Minimally Necessary Data Gap" is an alternate path, that takes the following actions: captures the transaction details, delivers an Missing Data response to the EHR Integration Software, identifies the submitted Institution ID and Member ID in the Get DSR Status Request, determines if the submitted Institution ID and EHR Patient ID match an Institution ID and EHR Patient ID for a previously submitted DSR Request. If "Match", primary path, processing continues at the next step, if "No Match", alternate path, take the following actions: captures the transaction details, delivers a "Matching Record Not Found" response to the EHR Integration Software, and identifies the status of the DSR Request (e.g., Completed/Ready, Completed/No Report, and Not Completed). It also formats a Get DSR Status Response and delivers the Get DSR Status Response to the EHR Integration Software initiating the Get DSR Status Request. The EHR Integration Software also receives the Get DSR Status Response.

Post-Conditions for the EHR Integration Software performed the following actions: determined it was time to deliver a Get DSR Status Request, formatted a Get DSR Status Request to the agreed upon specifications, initiated a secure communication with DSR Engine DCTS/DSR, received a handshake response indicating that the communication was authorized, delivered the Get DSR Status Request to DSR Engine DCTS/DSR, and received a Get DSR Status Response from DSR Engine DCTS/DSR.

The DSR Engine DCTS/DSR (post-conditions): authenticated a communication request, received a Get DSR Status Request, validated the Get DSR Status Request format, validated the Get DSR Status Request/Minimally Necessary data, matched the Institution ID and EHR Patient ID to existing DSR Request, identified the status of the DSR Request, formatted a Get DSR Status Response, and delivered a Get DSR Status Response to the EHR Integration Software originating the Get DSR Request.

A sixth example (e.g., use case #6) 413 (FIG. 4) describes how the EHR Integration Software initiates and delivers a Retrieve DSR Request to DSR Engine, how DSR Engine; authenticates the communication, accepts the Retrieve DSR Request, identifies the Institution ID and Member ID, determines the Practice ID and Member ID match an existing DSR Request for the same Practice ID and Member ID, identifies the Institution wants to receive the DSR via "Data", and delivers a Retrieve DSR Response to the EHR Integration Software, and how the EHR Integration Software receives the response, identifies the Patient, and populates a standard presentation form for this data.

Use Case #6 identifies processes that occur at DSR Engine DCTS/DSR and at the EHR Integration Software. The Get DSR Status Request/Response is a synchronous communication. DSR Engine will provide time interval guidance on when the EHR Integration Software should follow-up a Get DSR Status Request with a Retrieve a DSR Assumptions (i.e. dependencies that are external to the solution) supporting this Use Case include: authentication, authorization, and handshake rules established for EHR Integration Software and DSR Engine DCTS/DSR communications, EHR Integration Software previously submitted a DSR Request to DSR Engine, EHR Integration Software preceded this transaction with a Get DSR Status, institution ID and Member ID on the Get DSR Status Request matches the Institution ID and Member ID on a previously submitted DSR Request, and EHR Integration Software chose to make the DSR available as a PDF File.

Pre-Conditions (i.e. dependencies that are internal to the solution) supporting this Use Case includes: authentication processes co-implemented, and EHR Integration Software previously identified that they would receive a DSR as "discrete data".

In operation, the EHR Integration Software: formats a Retrieve DSR request using agreed upon specifications and the Institution ID and EHR Patient ID of a previously submitted DSR Request, and initiates secure communications with DSR Engine DCTS/DSR. The DSR Engine determines if the Retrieve DSR Request is an authentic transaction. If "Authentic" (a primary path), it takes the following actions: delivers an Authorized Request response to the EHR Integration Software, and awaits next communication. If "Not Authentic", an alternate path, it takes the following actions: captures the transaction details, and delivers an Unauthorized Request response to the EHR Integration Software. The EHR Integration Software receives the authentic handshake and delivers the Retrieve DSR Request to DSR Engine DCTS/DSR. The DSR Engine receives the Retrieve DSR Request and determines if the Retrieve DSR Request is properly formatted. If "Properly Formatted" (a primary path), it continues processing at the next step. "If Not Properly Formatted" (an alternate path), it take the following actions: captures the transaction details, delivers an Invalid Parameter response to the EHR Integration Software, and determines if the Retrieve DSR Request includes minimally necessary data. If it is "Minimally Necessary Data" (a primary path) continues processing at the next step.

If it is a "Minimally Necessary Data Gap" (an alternate path), it takes the following actions: captures the transaction details, delivers an Missing Data response to the EHR Integration Software, identifies the submitted Institution ID and EHR Patient ID, and determines if the submitted Institution ID and EHR Patient ID match an Institution ID and EHR Patient ID for a previously submitted DSR Request. If "Match", a primary path, the processing continues at the next step. If "No Match", an alternate path, it takes the following actions: captures the transaction details, delivers a "Matching Record Not Found" response to the EHR Integration Software, and identifies if the EHR/EHR Integrator wants DSRs delivered as "Discrete Data" or "PDF". For the "Discrete Data", primary path condition, it may continue processing at the next processing step, or if "PDF", an alternate path, it may alternatively use case #7 (Example 7), described below.

The DSR response may be formatted, and may include: Report Creation Date, total Annual Patient Savings, total Annual Total Savings, Patient First Name, Patient Last Name, Annual Patient Deductible, Pharmacy ID, Pharmacy Name, Pharmacy Street Address, total Savings, Current Medication Count, Current Medication Counter, Medication Name/Strength, Medication Dosage Form, Medication Quantity, Prescriber Last Name, Prescriber Phone Number, Annual Patient Savings, Annual Total Savings, Alternative Medication #1, Medication Name/Strength, Medication Dosage Form Medication Quantity, Annual Patient Savings, Annual Total Savings, Alternative Medication #2, Medication Name/Strength, Medication Dosage Form, Medication Quantity, Annual Patient Savings, Annual Total Savings, Alternative Medication #3, Medication Name/Strength, Medication Dosage Form, Medication Quantity.

Situational, Annual Patient Savings, Annual Total Savings. It also delivers the Retrieve DSR Response to the EHR/EHR Integrator initiating the Retrieve DSR Request. The EHR Integration Software also receives the Retrieve DSR Response with discrete data.

Post-Conditions for the EHR Integration Software include: formatted a Retrieve DSR Request to the agreed upon specifications, initiated a secure communication with DSR Engine DCTS/DSR, received a handshake response indicating that the communication was authorized, delivered the Retrieve DSR Request to DSR Engine DCTS/DSR, and received a Retrieve DSR Response from DSR Engine DCTS/DSR.

The DSR Engine DCTS/DSR also: authenticated a communication request; received a Retrieve DSR Request; validated the Retrieve DSR Request format; validated the Retrieve DSR Request/Minimally Necessary data; matched the Institution ID and Member ID to existing DSR Request; identified EHR/EHR Integrator preference for "Data"; formatted a Retrieve DSR Response; delivered a Retrieve DSR Response to the EHR Integration Software originating the Get DSR Request; and retrieve a DSR/PDF.

A seventh example (Use Case #7) describes how an EHR Integration Software initiates and delivers a Retrieve DSR Request to DSR Engine, how DSR Engine; authenticates the communication, accepts the Retrieve DSR Request, identifies the Institution ID and Member ID, determines the Practice ID and Member ID match an existing DSR Request for the same Practice ID and Member ID, identifies the Institution wants to receive the DSR via PDF, and delivers a Retrieve DSR Response to the EHR Integration Software, and how the EHR Integration Software receives the response, identifies the Patient, and links the PDF to the Patient in a standard location.

Use Case #7 substantially overlaps with example #6, above. In addition, the Get DSR Status Request/Response is a synchronous communication. DSR Engine will provide time interval guidance on when an EHR/EHR Integrator should follow-up a Get DSR Status Request with a Retrieve a DSR.

Assumptions (i.e. dependencies that are external to the solution) supporting this use Case are the same as in use case #6, above. EHR Integration Software chose to make the DSR available as formatted data.

Pre-Conditions (i.e. dependencies that are internal to the solution) supporting this use case includes: authentication processes co-implemented, and EHR/EHR Integrator previously identified that they would receive a DSR as a "PDF".

In use, the EHR Integration Software formats a Retrieve DSR request using agreed upon specifications and the Institution ID and Member ID of a previously submitted DSR Request, and initiates secure communications with DSR Engine DCTS/DSR. The DSR Engine DCTS/DSR: determines if the Retrieve DSR Request is an authentic transaction. If "Authentic", the primary path, it takes the following actions: delivers an Authorized Request response to the EHR Integration Software, and awaits next communication. If "Not Authentic", the alternate path, take the following actions: captures the transaction details, delivers an Unauthorized Request response to the EHR Integration Software.

The EHR Integration Software: receives the authentic handshake, and delivers the Retrieve DSR Request to DSR Engine DCTS/DSR.

The DSR Engine DCTS/DSR: receives the Retrieve DSR Request; determines if the Retrieve DSR Request is properly formatted. If "Properly Formatted", the primary path, continues processing at the next step. If "Not Properly Formatted", the alternate path, it take the following actions: captures the transaction details; delivers an Invalid Parameter response to the EHR Integration Software; determines if the Retrieve DSR Request includes minimally necessary data. If "Minimally Necessary Data", the primary path, it continues processing at the next step. If "Minimally Necessary Data Gap", the alternate path, take the following actions: captures the transaction details, delivers an Missing Data response to the EHR Integration Software, identifies the submitted Institution ID and Member ID, determines if the submitted Institution ID and Member ID match an Institution ID and Member ID for a previously submitted DSR Request. If "Match", the primary path, processing continues at the next step. If "No Match", alternate path, take the following actions: captures the transaction details, does not respond to the transaction, and identifies if the EHR/EHR Integrator wants DSRs delivered as "PDF" or "Data". If "PDF", the primary path, it continue processing at the next processing step. If "Data", alternate path, alternate use case (e.g., use case #6). It also formats a DSR per Payer defined specifications, formats a Retrieve DSR Response (Format T.B.D.) including the PDF, and delivers the Retrieve DSR Response to the EHR/EHR Integrator initiating the Retrieve DSR Request.

The EHR/EHR Integrator: receives the Retrieve DSR Response with an attached PDF. The Post-Conditions for the EHR Integration Software: formatted a Retrieve DSR Request to the agreed upon specifications, initiated a secure communication with DSR Engine DCTS/DSR, received a handshake response indicating that the communication was authorized, delivered the Retrieve DSR Request to DSR Engine DCTS/DSR, and received a Retrieve DSR Response from DSR Engine DCTS/DSR.

The DSR Engine DCTS/DSR: authenticated a communication request; received a Retrieve DSR Request; validated the Retrieve DSR Request format; validated the Retrieve DSR Request/Minimally Necessary data; matched the Institution ID and Member ID to existing DSR Request; identified EHR/EHR Integrator preference for "PDF"; formatted a Retrieve DSR Response, and delivered a Retrieve DSR Response, with attached "PDF", to the EHR Integration Software originating the Get DSR Request.

In example 8 (use case #8 419, FIG. 4) the methods and apparatuses described herein may be used to deliver a Post Encounter Medication List to the DSR Engine. Use case #8 may be used to describe how the EHR/EHR Integration Software: identifies Participating Patients and their medication list after a Patient encounter; formats a DSR Post Encounter Medication List, and delivers the DSR Post Encounter Medication List to DSR Engine DCTS/DSR, how DSR Engine DCTS/DSR receives the DSR Post Encounter Medication List and captures the data.

In this example, use case #8 identifies processes and software that are supported by the EHR/EHR Integration Software and DSR Engine. As a default, the DSR Engine proposes that the creation and delivery of the Post Encounter Medication List occur two days after a DSR is retrieved.

Assumptions (i.e. dependencies that are external to the solution) supporting this example includes: the EHR/EHR Integration Software has presented the DSR as "PDF File" (i.e. use case #7). The EHR Integration Software can identify when a Patient has completed a visit, or it automatically initiates the process of identifying the medication list at an agreed upon time interval. The EHR Integration Software may only deliver a DSR Post Encounter Medication List if we previously delivered a DSR. Pre-Conditions (i.e. dependencies that are internal to the solution) supporting this Use Case may include: authentication processes co-implemented.

In use, the EHR Integration Software: determines an encounter (visit) has occurred for a Participating Patient, and captures Patient attribute data. For example, the attribute may include one or more of: Participating Payer ID, Patient First Name, Patient Last Name, Patient Date of Birth, Patient Gender Code, Medical Benefit/Member ID, Rx Benefit/BIN Number, Rx Benefit/Processor Control Number, Rx Benefit/Group ID (Varies by Payer), Rx Benefit/Cardholder ID, and Patient's Preferred Pharmacy. The software may also identify the current medication history for each Participating Patient, including: Prescriber ID: [NPI], Prescriber Last Name, Medication ID (e.g., RxNorm or Representative NDC), Quantity, and/or Days' Supply. It may also format a DSR Post Encounter Medication List for the Participating Patient/Encounter using agreed upon specifications and the Institution ID and Member ID of a previously submitted DSR Request. It may also initiate secure communications with DSR Engine DCTS/DSR. For example, a DSR Engine DCTS/DSR: determines if the DSR Post Encounter Medication List is an authentic transaction. If "Authentic", a primary path, it takes the following actions: delivers an Authorized Request response to the EHR Integration Software, and awaits next communication. If "Not Authentic", an alternate path, it takes the following actions: captures the transaction details, and delivers an Unauthorized Request response to the EHR Integration Software.

The EHR Integration Software in this example receives an "Authentic" handshake, and delivers the DSR Post Encounter Medication List to DSR Engine DCTS/DSR. The DSR Engine DCTS/DSR: receives the DSR Post Encounter Medication List, formats a DSR Post Encounter Medication List Response, and delivers the DSR Post Encounter Medication List Response to the EHR Integration Software delivering the request. The EHR Integration Software may receive an "Accepted" response.

In the post-condition in this example, the EHR Integration Software: determined an encounter had occurred for a Participating Patient, identified the medication history for the Patient, formatted a DSR Post Encounter Medication List to the agreed upon specifications, initiated a secure communication with DSR Engine DCTS/DSR, received a handshake response indicating that the communication was authorized, delivered the DSR Post Encounter Medication List to DSR Engine DCTS/DSR, and received an "Accepted" response from DSR Engine DCTS/DSR.

The DSR Engine DCTS/DSR: authenticated a communication request the EHR Integration Software, received a Retrieve DSR Request, and delivered an "Accepted" Response to the EHR Integration Software.

Example 9 (use case #9 417, FIG. 4) is an example of a identifying an Alternative Medication Selection to the DSR Engine. Use case #9 describes how the EHR/EHR Integration Software: identifies when the Prescriber has ordered a DSR presented Alternative Medication, formats a DSR Alternative Medication Selection, and delivers the DSR Alternative Medication Selection to DSR Engine DCTS/DSR, how DSR Engine DCTS/DSR receives the DSR Alternative Medication Selection and captures the data. Use case #9 identifies processes and software that are supported by the EHR/EHR Integration Software and DSR Engine. As a default, the DSR Engine proposes that the creation and delivery of the Alternative Medication Selection as soon as it is known.

Assumptions (i.e. dependencies that are external to the solution) supporting this use case include: the EHR/EHR Integration Software has presented the DSR as "Data" (i.e. Use Case #6, above). The EHR/EHR Integration Software can detect with the Prescriber has selected a presented Alternative Medication. The EHR/EHR Integration Software may only deliver a DSR Alternative Medication Selection if we previously delivered a DSR. The Alternative Medication Selection transaction is a one Patient/one medication transaction.

Pre-Conditions (i.e. dependencies that are internal to the solution) supporting this Use Case include authentication processes co-implemented.

In use, the EHR Integration Software: determines the Prescriber has selected a DSR presented Alternative Medication and captures the following data. The data may include: Institution ID, Participating Payer ID, Patient First Name, Patient Last Name, Patient Date of Birth, Patient Gender Code, Medical Benefit/Member ID, Rx Benefit/BIN Number, Rx Benefit/Processor Control Number, Rx Benefit/Group ID (Varies by Payer), Rx Benefit/Cardholder ID, Patient's Preferred Pharmacy, Prescriber ID:, Prescriber Last Name, Medication ID (e.g., RxNorm and/or Representative NDC), Quantity, Days' Supply, and DSR Engine Transaction ID.

The EHR Integration Software may also format a DSR Alternative Medication Selection transaction using agreed upon specifications, and initiates secure communications with the DSR Engine DCTS/DSR. For example, the DSR Engine DCTS/DSR: determines if the DSR Alternative Medication Selection transaction is authentic. If "Authentic", a primary path, takes the following actions: delivers an Authorized Request response to the EHR Integration Software, and awaits next communication. If "Not Authentic", an alternate path, it may take the following actions: captures the transaction details, and delivers an Unauthorized Request response to the EHR Integration Software.

The EHR Integration Software may receive an "Authentic" handshake. This may deliver the DSR Alternative Medication Selection to DSR Engine DCTS/DSR. The EHR Integration Software: determined the Prescriber selected a presented Alternative Medication, formatted a DSR Alternate Medication Selection, initiated a secure communication with DSR Engine DCTS/DSR, received a handshake response indicating that the communication was authorized, and delivered the DSR Alternate Medication Selection to DSR Engine DCTS/DSR.

The DSR Engine DCTS/DSR: authenticated a communication request to the EHR Integration Software, and received a DSR Alternate Medication Selection Request.

As used herein, the following acronyms may refer to: Automated Alternatives Analysis (AAA), Configurable Alternatives Engine (CAE), Cost Transparency (CT), Drug Cost Transparency Services (DCTS), Drug Savings Report, (DSR), Electronic Health Record (EHR), Configurable Alternatives Engine (CAE), National Prescriber Identifier (NPI), Prior Authorization (PI), Pharmacy Benefit Manager (PBM), Portable Document Format (PDF, e.g., Adobe Acrobat), and Uniform Resource Locator (URL).

As used herein, DSR or Blue DSR may refer to the Automated Alternatives Analysis output that is delivered to the EHR/EHR Integrator. The DSR Request may refer to the transaction that the EHR/EHR Integrator delivers to DSR Engine that initiates DSR processing. The Alternate Pharmacy (Alt. Pharmacy) may refer to a pharmacy other than the Submitted Pharmacy. Alternate Pharmacies are identified by the PBM. Also referred to as Alternate Fulfillment. The Alternative Medication(s) or Alternative Therapy may refer to a drug(s) that has the same or similar effect in the treatment of a disease or condition as the Existing Medication. The Aggregated Annual Patient Savings may refer to the estimated financial savings, between the Existing Medication and an Alternative Medication, which the Patient can expect to receive if they convert to the identified Alternative Medications. When more than one Alternative Medication is identified, the Aggregated Annual Patient Savings calculations may use the Alternative Medication with the greatest Patient Savings. The Aggregated Annual Total Savings may refer to the estimated financial savings, between the Existing Medication and an Alternative Medication, which the Patient and Payer can expect to receive if they convert to the identified Alternative Medications. When more than one Alternative Medication is identified, the Aggregated Annual Total Savings calculations may use the Alternative Medication with the greatest total Savings. Annual Patient Savings may refer to the estimated financial savings, between the Existing Medication and an Alternative Medication, which the Patient can expect to receive if they convert to the Alternative Medication.

Annual Total Savings may refer to the estimated financial savings, between the Existing Medication and an Alternative Medication, which the Patient and Payer can expect to receive if they convert to the Alternative Medication. Approved CT Response may refer to the response that is delivered to the EHR when an Existing Medication or previously prescribed medication is approved by the pharmacy claims processor. A Cardholder ID may refer to the pharmacy benefit ID assigned to the cardholder or pharmacy identification number used by the plan. Chosen Medication may refer to the medication selected by the Prescriber and delivered to GH in a Cost Transparency Request. Chronic Care Medication may refer to drugs that are commonly used to treat conditions that are considered chronic or long-term. These conditions usually require regular, daily use of medicines. Configurable Alternatives Engine may refer to the DCTS software that identifies Alternative Medications and aligns the identified medications with Payer's formulary, including indicators for Preferred Medications and Excluded Medications. Cost Transparency Request may refer to the inbound transaction delivered to DSR Engine from the EHR that initiates the Cost Transparency process event. The cost Transparency Response may refer to the outbound transaction delivered to the EHR from Configurable Alternatives Engine that completes the Cost Transparency process event. The Coverage Gap may refer to the Medicare Part D benefit structure that indicates a coverage period or amount is ended and gap (i.e. donut hole) before another coverage period or amount begins. The Day's Supply may refer to the estimated number of days a medication order will last. A Deductible may refer to an amount that is collected from the Patient before coverage begins. Drug Cost Transparency Services may refer to a term describing the Configurable Alternatives Engine services. Otherwise recognized as a Real-Time Prescription Benefit service. Estimated Patient Reward may refer to a projected and incremental Patient savings if the Patient replaces the current medication with an alternative medication.

Existing Medication(s) may refer to a drug from the Patient's medication list and identified in the DSR Request. Member ID may refer to the medical benefit ID assigned to the cardholder or medical identification number used by the plan. Minimum Aggregated Annual Patient Savings Threshold may refer to configuration parameter(s) defined by the Payer, rather than the Healthcare System/Prescriber Group, that identifies the threshold for minimum Annual Patient Savings for the collection of identified Alternative Medications. Either the Minimum Aggregated Annual Patient Savings Threshold or the Minimum Aggregated Annual Total Savings Threshold condition may be met to present a DSR. A Minimum Aggregated Annual Total Savings Threshold may refer to configuration parameter(s) defined by the Payer, rather than the Healthcare System/Prescriber Group, that identifies the threshold for minimum Annual Total Savings for the collection of identified Alternative Medications. Either the Minimum Aggregated Annual Patient Savings Threshold or the Minimum Aggregated Annual Total Savings Threshold condition must be met to present a DSR. A Participating Payer may refer to an organization, responsible for the financing and/or reimbursement of healthcare service, which has contracted with GH for DSR.

The Patient Cost may refer to the "Patient Cost" is the estimated Patient financial responsibility for the following: existing Medication & Quantity at the Submitted Pharmacy, alternative Medication(s) & Quantity at the Submitted Pharmacy, existing Medication & Extended Days Quantity at an Alternate Pharmacy, or existing Medication & Quantity via Drug Savings Card. The total Cost may refer to the "total Cost" is the combination of the estimated Patient financial responsibility and the Payer financial responsibility. Patient Rewards may refer to the incremental incentives that motivate a Patient to move from a Current Medication to an Alternative Medication. The Payer may refer to the organization at risk for a portion of Patient's pharmacy benefits. The PBM Request may refer to the outbound transaction delivered to a PBM from Configurable Alternatives Engine. The PBM Request may be a Billing, Pre-Determination of Benefits, or a proprietary transaction. A PBM Response may refer to the inbound transaction delivered to Configurable Alternatives Engine from a PBM. The PBM Response may be "Approved" or "Denied". A Prescriber may refer to a person licensed to order (prescribe) medications. Prior Authorization may refer to a managed care process used to control the costs and risks posed by prescription drugs. The process determines if the health plan will cover a prescribed medication. The Quantity or Medication Quantity may refer to the number of medication billing units that are used to determine the Patient and Payer costs.

A Rejected CT Response may refer to the response that is delivered to the EHR when an Existing Medication or previously prescribed medication is rejected by the pharmacy claims processor. Remaining Medication may refer to the Existing Medications that are left after they have been optionally filtered to exclude Acute Care, Preferred, and Lowest Tier medications. A Representative NDC may refer to one of any 11-digit NDC codes belonging to the same product concept that is nationally available, not repackaged, not obsolete, not private label, and not unit dose (unless it is the only NDC available). A product concept describes a medication or non-medication that has the same active ingredient, strength, route, dosage form, drug delivery system or packaging, and therapeutic use/indication. Product concepts also have brand and generic distinctions. For example, one product concept may be uniquely associated with a brand product, while another product concept may be uniquely associated with a generic version of the product. An RxNorm may refer to a National Institute Health service that provides normalized names for clinical drugs. Submitted Pharmacy may refer to the pharmacy presented to Configurable Alternatives Engine in the Cost Transparency Request.

Example 10: Dsr

Figure 5:
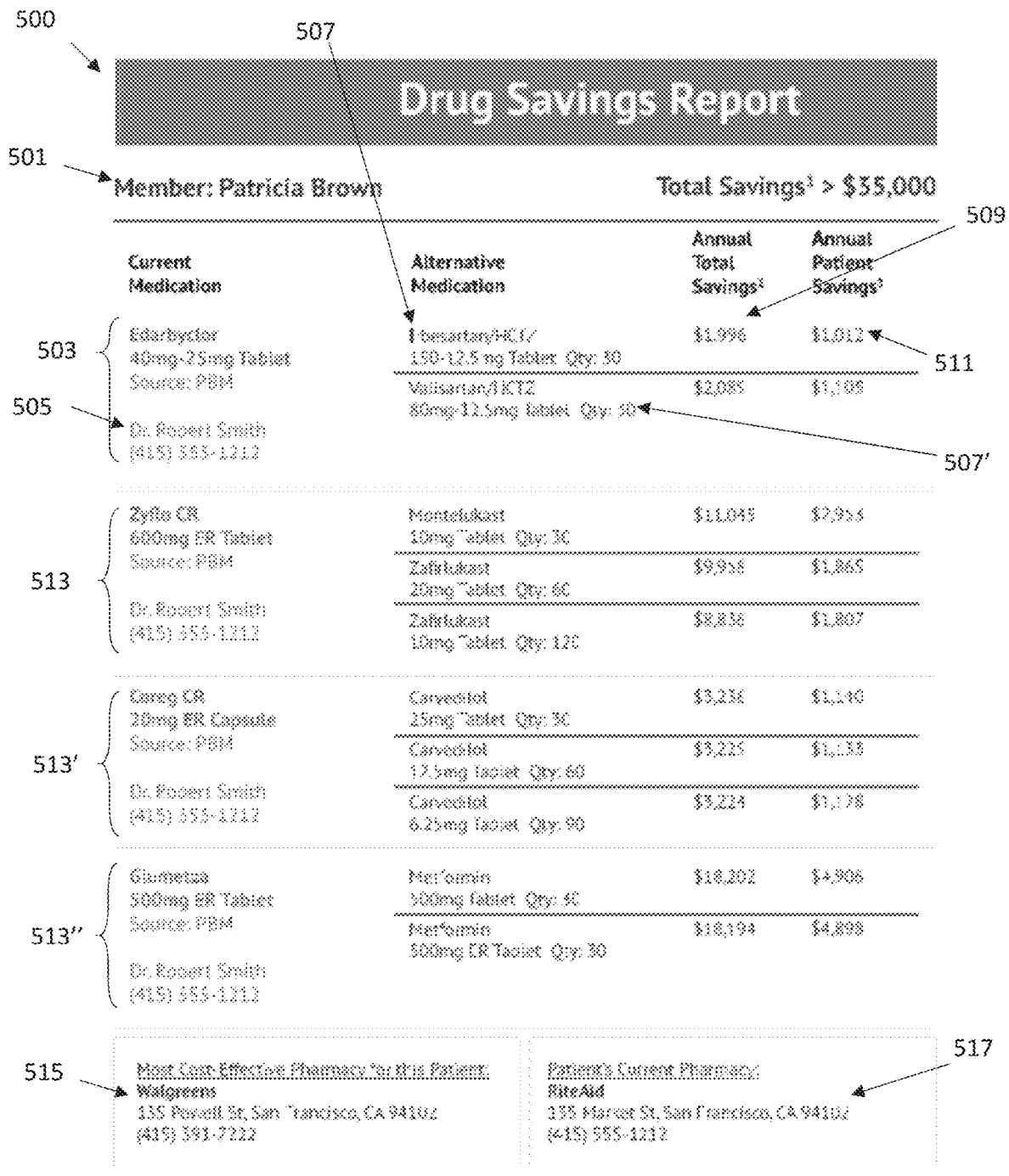
FIG. 5 is a first example of a DSR (DSR).

FIG. 5 illustrates a first example of a drug saving report 500 (DSR) as described herein. In this example, the DSR includes a patient by name 501. The DSR includes a listing of the patient's current medications 503, 513, 513', 513", indicating which Prescriber 505 prescribed the medication. This information also includes the dosage, dose form and the source from which the drug was identified to generate the report. For each of the patient's current medications, a second column indicates a therapeutically equivalent alternative medication(s) 507, 507', and also indicating the dosage and dose form for each. Additional columns indicate for each alternative medication an annual total savings 509 if the patient were to switch to the alternative medication as well as an annual patient savings 511 if the patient were to switch to the alternative medication. In this example, the patient has four preexisting medications shown (additional preexisting medications may be included on other pages), and two or three therapeutically equivalent medications are shown, along with associated cost savings (total savings and patient savings), shown as annualized amounts. In additional the report also indicates the patient's current pharmacy 517 and alternate pharmacy 515 that is near the patient's address but could be more cost-efficient for the patient. In this example, as shown by the notes on the bottom of the report, the estimated total cost savings are based on fulfillment at the Patient's current pharmacy. The estimated annual total savings are based on the Patient's current pharmaceutical insurance coverage, as is the estimated annual patient savings. The estimated total and patient savings may be indicated as "greater than" a particular value (see, e.g., FIG. 8), or as a range of values (e.g., between x$ and y$), rather than as precise values. In some variations only the patient saving is shown; alternatively, in some variations, only the total savings is shown.

Figure 6:
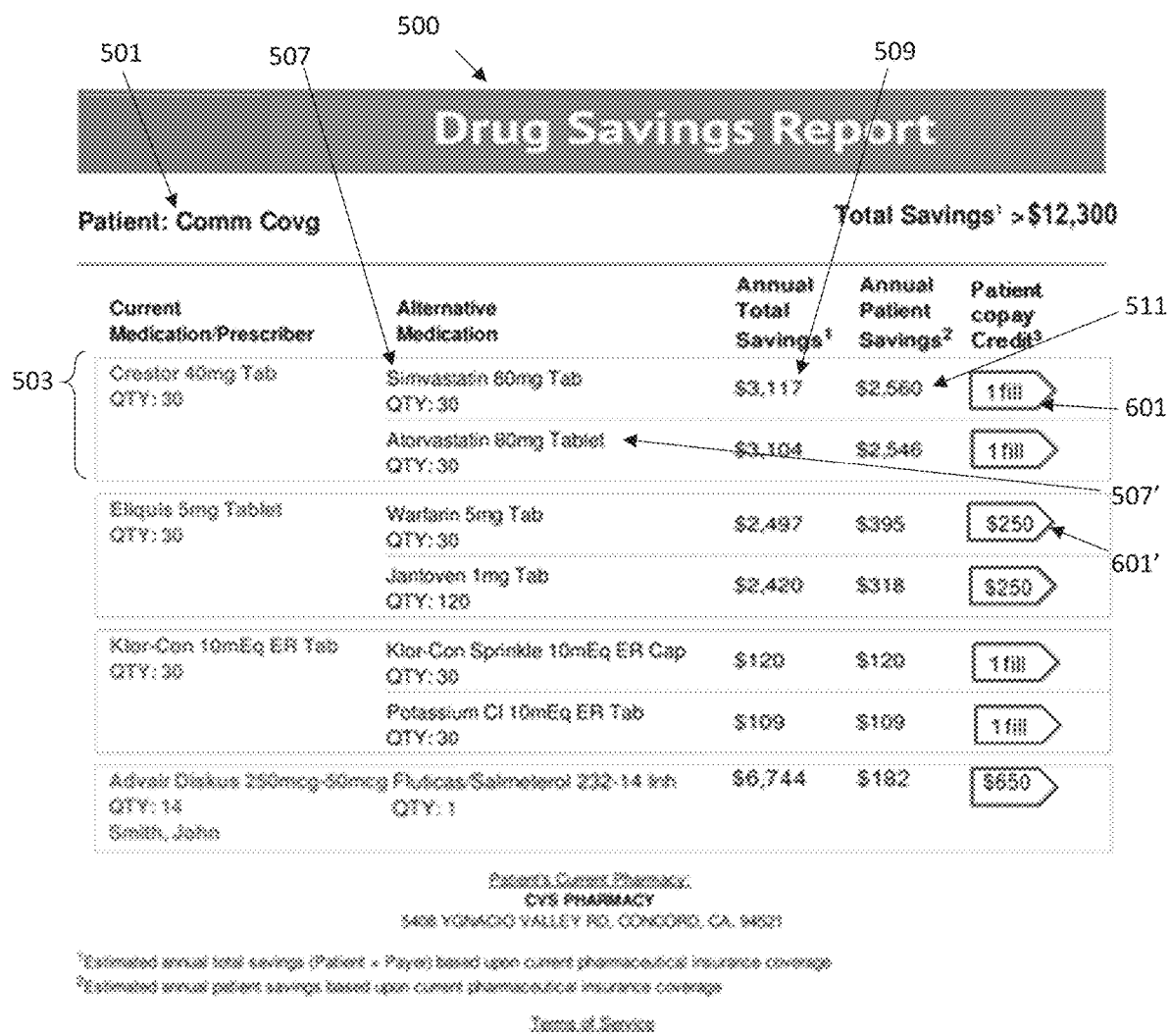
FIG. 6 is another example of a DSR.

As described above, any of these methods and apparatuses may be configured to incentivize a patient to switch to a lower cost medication. It has been found that in some cases, merely seeing the hypothetical savings may not be sufficient for the Patient to switch to the lower-cost therapeutically equivalent medication, particularly in instances where the savings to the patient are low (even where overall savings are high) or in instances where the patient has recently fulfilled a prescription and may not want to switch. However, in such cases the Payer may include one or more incentives to more strongly motivate the Patient to switch. In particular, in instances where the total cost savings (e.g., total annual cost savings) are high compared to the patient cost savings (e.g., annual patient cost savings), the Payer may select to provide one or more incentives, such as a copayment credit, rebate, etc. FIG. 6 illustrates an example of a PSR similar to that in FIG. 5 in which an incentive credit is provided by the Payer; the incentive credit may be calculated as described herein.

In FIG. 6, the customized DSR 500 includes the patient's name 501, a listing of current preexisting medications 503, dosage/dose form (and the name of a Prescriber, if known) as well as any therapeutically equivalent alternative medications 507, 507'. The report also includes a total savings, shown as total annual savings 509 in this example, and patient savings, shown as total patient savings 511. As shown in FIG. 6, the Payer may select to allow incentive credits 601, 601' to be provided to the patient base on a set of incentive credit rules that the Payer may specify/approve. For example, in some variations, if the total savings are greater than a Payer-selected (or default) amount and/or if the total savings is greater than annual patient savings by a Payer-selected (or default) amount, a credit may be applied; the type and/or amount of the credit may be selected of set as a set of rules to be applied by the CAE. For example, in FIG. 6, the incentive credit for both of the therapeutically effective alternative medications for the first medication 503 are presented as "1 fill" meaning that the patient may fill the initial prescription for free. Alternatively, in some variations (noticeably those having a total savings of greater than $1000 more than the patient savings), a copay credit 601' that is approximately 10% of the annual total savings is provided (e.g., offered by the DSR).

Alternatively or additionally, in some variations 9 as shown in FIG. 7, the incentive credit may be a cash-value coupon 701. In this example, the couple incentivizes the patient to switch pharmacies, e.g., to a lower-cost pharmacy, by providing $90 cash credit.

FIGS. 8 and 9 illustrate alternative examples of drug saving reports in which the estimated annual total savings and estimated annual patient savings are greater than some value. In FIG. 9, the Payer rules for determining if and what incentive credit (e.g., patient copay credit) to apply are more stringent than in FIG. 6; a copay credit is provided only for the second-listed preexisting patient medication, and a flat credit of 250 is offered. In this case, the patient incentive credit is offered only when the annual patient savings is less than a minimum threshold (e.g., $100) and the total annual savings is greater than the annual patient savings by a second minimum threshold (e.g. $500).

In any of these examples, the DSR may also indicate the source of the preexisting medication, as mentioned above. For example, an alphanumeric codes may be included associated with the current medication (e.g., a "C", for "chart" may indicate that the medication was identified from the Patient's EMR, a "P" may indicate that the medication was identified from the Payer database, etc.).

Example 11: Estimation of Annual Patient Cost Savings

The annual cost savings to the patient may be estimated as annual cost savings. Any of the methods and apparatuses described herein may estimate the cost savings to the patient. For example, a patient saving report generation engine and PBM request module may estimate an annual patient cost savings from a list of therapeutically equivalent alternative medications. In some variation the method and/or apparatus may determine if the amount applied to the periodic deductible is greater than zero. If populated & greater than $0, discontinue Annual Patient Savings calculations. If "Not Available, Not Populated, or Populated with $0", continue Annual Patient Savings calculations at the next processing step. The engine may determine if the Amount Attributed to Coverage Gap is populated with a value greater than "Zero". If "Populated & Greater than $0", discontinue Annual Patient Savings calculations. If "Not Available, Not Populated, or Populated with $0", continue Annual Patient Savings calculations at the next processing step. To calculate an annual patient cost for the First/Next Existing Medication, identify the following information for the First/Next Existing Medication: amount of Copay (518-FI), amount of Co-Insurance (572-4U), a days' Supply (405-D5), determine if the Patient's benefit structure is a copay or co-insurance; determine the amount of Copay, or the amount of Co-Insurance. Then calculate a Patient Cost per Day for the First/Next Existing Medication: e.g., Patient Cost divided by Days' Supply=Patient Cost per Day, then calculate a Patient Cost per Year for the First/Next Existing Medication: Patient Cost per Day (X) 365 (Days in a Year)=Patient Cost per Year. Then calculate an Annual Patient Cost for the First/Next Alternative Medication. First identify the following Information for the First/Next Alternative Medication, the amount of Copay (518-FI), an amount of Co-Insurance (572-4U), and a Days' Supply (405-D5). Then determine if the Patient's benefit structure is a copay or co-insurance (e.g., from the Amount of Copay, or Amount of Co-Insurance, calculate a Patient Cost per Day for the First/Next Alternative Medication, Patient Cost divided by Days' Supply=Patient Cost per Day). Next calculate a Patient Cost per Year for the First/Next Alternative Medication: Patient Cost per Day (X) 365 (Days in a year)=Patient Cost per Year. Then calculate an Annual Patient Savings for the First/Next Alternative Medication: the Annual Patient Cost for the First/Next Existing Medication minus the annual Patient Cost for the First/Next Alternative Medication=Annual Patient Savings.

Example 12: Estimation of Annual Total Cost Savings

The annual total savings to the patient may be estimated as annual cost savings. Any of the methods and apparatuses described herein may estimate the cost savings to the patient. For example, as in the previous example, the PBM may be queried to identify cost information for each drug and patient-specific information. For example, the methods and apparatuses described herein may calculate a total Cost for the First/Next Existing Medication. In some examples, the method/apparatus may identify the following information for a First/Next Existing Medication: patient Pay Amount (505-F5), total Amount Paid (509-F9), Days' Supply (405-D5). The methods/apparatus may then calculate a total Cost for the First/Next Existing Medication, e.g., from Patient Pay Amount+total Amount Paid=total Cost. The method/apparatus may then calculate a total Cost per Day for the First/Next Existing Medication, e.g., from total Cost divided by Days' Supply=total Cost per Day.

The method/apparatus may then calculate a total Cost per Year for the First/Next Existing Medication. For example, the total cost per year may be estimated from: cost per Day times 365 (Days in a Year)=total Cost per Year. A total Cost for the First/Next Alternative Medication may also be estimated. For example, the method/apparatus may identify the following Information for the First/Next Alternative Medication: Patient Pay Amount (505-F5), total Amount Paid (509-F9), and Days' Supply (405-D5). Total Cost per Day for the First/Next Alternative Medication may then be calculated, e.g., by dividing the total Cost by Days' Supply=total Cost per Day. The total Cost per Year for the First/Next Alternative Medication may then be calculated. The Cost per Day times 365 (Days in a Year)=total Cost per Year. The total Savings for the First/Next Alternative Medication may be calculated from the total Cost for the First/Next Existing Medication minus the total Cost for the First/Next Alternative Medication=Annual Total Savings.

Example 13: Estimation of Annual Patient Savings/BSC

The annual patient savings may be estimated as an annual Patient Savings Calculation/BSC. The PBM may be used to determine estimates for cost of specific therapeutically equivalent medications. For example the method/apparatus may determine if the Amount Applied to Periodic Deductible is populated with a value greater than "Zero". If "Populated & Greater than $0", discontinue Annual Patient Savings calculations, if "Not Available, Not Populated, or Populated with $0", continue Annual Patient Savings calculations at the next processing step. Next, determines if the Amount Attributed to Coverage Gap is populated with a value greater than "Zero". If "Populated & Greater than $0", discontinue Annual Patient Savings calculations, otherwise if "Not Available, Not Populated, or Populated with $0", continue Annual Patient Savings calculations at the next processing step. An Annual Patient Cost for the First/Next Existing Medication may be scheduled following this. The method/apparatus may then identify the following information for the First/Next Existing Medication: Patient Pay Amount (Field FQ, Occurrence #1, Positions 12-19), Days' Supply (Field FQ, Occurrence #1, Positions 30-32), and may calculate a Patient Cost per Day for the First/Next Existing Medication from: Patient Pay Amount divided by Days' Supply=Patient Cost per Day. The method/apparatus may then calculate a Patient Cost per Year for the First/Next Existing Medication: Patient Cost per Day times 365 (Days in a Year)=Patient Cost per Year. The method/apparatus may then calculate an Annual Patient Cost for the First/Next Alternative Medication, including Identifying the following Information for the First/Next Alternative Medication, determining the patient Pay Amount (Field FQ, Occurrence #1, Positions 12-19), and Days' Supply (Field FQ, Occurrence #1, Positions 30-32), then calculate a Patient Cost per Day for the First/Next Alternative Medication: e.g., Patient Pay Amount divided by Days' Supply=Patient Cost per Day; then calculate a Patient Cost per Year for the First/Next Alternative Medication: Patient Cost per Day X (times) 365 (Days in a year)=Patient Cost per Year.

The method and apparatus may then calculate an Annual Patient Savings for the First/Next Alternative Medication: an annual Patient Cost for the First/Next Existing Medication minus the Annual Patient Cost for the First/Next Alternative Medication=Annual Patient Savings.

Example 14: Estimation of Annual Total Savings/BSC

The annual total savings may be estimated, for example, from a calculation of a total Cost for the First/Next Existing Medication. For example, the method/apparatus may: Identify the following information for the First/Next Existing Medication, e.g., from total Cost (Field FQ, Occurrence #1, Positions 34-40) and the Days' Supply (Field FQ, Occurrence #1, Positions 30-32). The method/apparatus may then calculate a total Cost per Day for the First/Next Existing Medication, e.g., total Cost divided by Days' Supply=total Cost per Day. The method/apparatus may also estimate a total Cost per Year for the First/Next Existing Medication from: Cost per Day X (times) 365 (Days in a Year)=total Cost per Year.

Further, the method/apparatus may calculate a total Cost for the First/Next Alternative Medication by Identifying the following Information for the First/Next Alternative Medication: total Cost (Field FQ, Occurrence #1, Positions 34-40), Days' Supply (Field FQ, Occurrence #1, Positions 30-32), and may then Calculate a total Cost per Day for the First/Next Alternative Medication from: total Cost divided by the Days' Supply=total Cost per Day. The total Cost per Year for the First/Next Alternative Medication may be calculated from the: Cost per Day X (times) 365 (Days in a Year)=total Cost per Year. Then calculate a total Savings for the First/Next Alternative Medication. The total Cost for the First/Next Existing Medication minus the total Cost for the First/Next Alternative Medication=Annual Total Savings.

Example 15: Estimation of Annual Total Savings/BSC

As mentioned above, any of the methods and apparatuses described herein may be configured to determine an estimate patient reward (e.g., incentive credit/reward). In one example, the apparatus/method may estimate a patient reward by: identifying the total Savings for the Existing Medication/Alternative Medication, identifying the Participating Payer (e.g., BIN Number, or BIN Number and Processor Control Number), then identifying the Participating Payer's: "Estimated Patient Reward Percent", then multiplying the total Savings by Estimated Patient Reward Percent".

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method of providing alternatives for one or more preexisting prescribed medications, the method comprising:

receiving, in a configurable alternatives engine (CAE), a request for an evaluation of a patient's preexisting prescribed medications following a triggering event comprising scheduling a patient appointment with a Prescriber, wherein the patient has a Payer responsible for financing health care services for the patient;

generating a patient-specific datastore including a set of the patient's preexisting prescribed medications;

identifying, from a Payer Preferred Alternative Medications Database, one or more therapeutically equivalent alternative medications corresponding to one or more of the patient's preexisting prescribed medications in the set of the patient's preexisting prescribed medications based on a clinical equivalency;

adding the therapeutically equivalent alternative medications to the patient-specific datastore;

rank-ordering the therapeutically equivalent alternative medications in the patient-specific datastore based on rules specific to Payer and Prescriber preferences;

building, in the CAE, a query for a pharmacy benefit manager (PBM) from a subset of the rank-ordered therapeutically equivalent alternative medications in the patient-specific datastore;

querying the PBM with the query to get a patient cost and a total cost associated with the subset of the therapeutically equivalent alternative medications, wherein the total cost includes both an estimated patient financial responsibility and an estimated Payer financial responsibility;

calculating a patient's savings and a total saving for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication; and offering, in a drug savings report (DSR), alternatives for the patient's preexisting prescribed medications, wherein the DSR shows: the patient's savings for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication.

2. The method of claim 1, wherein the rules specific to the Payer and Prescriber preferences include one or more of: formulary tiers, preferred medications, and excluded medications.

3. The method of claim 1, wherein identifying the one or more therapeutically equivalent alternative medications comprises estimating a clinically equivalent dose for each therapeutically equivalent alternative medication, wherein the clinically equivalent dose corresponds to the patient's dose of the corresponding preexisting prescribed medication.

4. The method of claim 1, wherein identifying the one or more therapeutically equivalent alternative medications comprises identifying three or more therapeutically equivalent alternative medications, wherein at least two of the therapeutically equivalent alternative medications comprise a Payer preferred equivalent medication and at least one of the therapeutically equivalent alternative medications comprises a Prescriber's preferred equivalent medication.

5. The method of claim 1, further comprising providing the DSR to the Prescriber and the patient.

6. The method of claim 1, wherein the DSR shows the total savings for each of the therapeutically equivalent alternative medications corresponding to each of the patient's preexisting prescribed medications that has a lower cost than the corresponding preexisting prescribed medication.

7. The method of claim 1, wherein calculating the patient's savings and the total savings comprises calculating an annual patient's savings and an annual total savings.

8. The method of claim 1, wherein the rules specific to the Payer and Prescriber preferences include minimum threshold amounts to present the alternative medication for one or more of: patient cost savings and total savings.

9. The method of claim 1, wherein the triggering event further comprises is one or more of: the Prescriber requests evaluation of existing patient medications or the patient requests evaluation of existing medications.

10. The method of claim 1, wherein collecting the patient cost and total cost includes collecting a patient cost and total cost associated with each of the patient's one or more preexisting prescribed drugs and the one or more alternative drugs at an alternative pharmacy.

11. A computer-implemented method of providing alternatives for one or more preexisting prescribed medications, the method comprising:

receiving, in a configurable alternatives engine (CAE), a request for an evaluation of a patient's preexisting medications following a triggering event comprising one or more of: scheduling a patient appointment with a Prescriber, Prescriber requests evaluation of existing patient medications or the patient requests evaluation of existing medications; wherein the patient has a Payer responsible for financing health care services for the patient;

generating a patient-specific datastore including a set of the patient's preexisting prescribed medications from one or more of: an electronic health record (EHR) associated with the patient and a database of patient pharmacy claims for the patient, and medication information provided by the patient;

identifying, from a Payer Preferred Alternative Medications Database and a Prescriber Preferred Database including rules specific to the Payer and Prescriber preferences, one or more therapeutically equivalent alternative medications corresponding to each of the patient's preexisting prescribed medications in the set of the patient's preexisting prescribed medications based on a clinical equivalency;

adding the therapeutically equivalent alternative medications to the patient-specific datastore;

rank-ordering the therapeutically equivalent alternative medications in the patient-specific datastore based on rules specific to the Payer and Prescriber preferences and removing equivalent alternative medications below a threshold rank from the patient-specific datastore;

building, in the CAE, a query for a pharmacy benefit manager (PBM) from a subset of the rank-ordered therapeutically equivalent alternative medications in the patient-specific datastore;

querying the PBM with the query to get a patient cost and a total cost associated with each of the patient's preexisting prescribed medications, and a patient cost associated and a total cost associated with the subset of the therapeutically equivalent alternative medications, wherein the total cost includes both an estimated patient financial responsibility and an estimated Payer financial responsibility;

calculating a patient's savings and a total saving for each of the therapeutically equivalent alternative medications in which at least one of: the patient cost of the therapeutically equivalent alternative medication is lower than the patient cost of the corresponding preexisting prescribed medication or the total cost of the therapeutically equivalent alternative medication is lower than the total cost of the corresponding preexisting prescribed medication; and offering, in a drug savings report (DSR) alternatives for the patient's preexisting prescribed medications, wherein the DSR shows:
- each of the patient's preexisting prescribed medications,
- any therapeutically equivalent alternative medications corresponding to each of the patient's preexisting prescribed medications that have a lower patient cost, a lower total cost or both a lower patient cost and total cost than the corresponding preexisting prescribed medication.

12. The method of claim 11, wherein the rules specific to the Payer and Prescriber preferences include one or more of: formulary tiers, preferred medications, and excluded medications.

13. The method of claim 11, wherein identifying the one or more therapeutically equivalent alternative medications comprises estimating a clinically equivalent dose for each therapeutically equivalent alternative medication, wherein the clinically equivalent dose corresponds to the patient's dose of the corresponding preexisting prescribed medication.

14. The method of claim 11, wherein identifying the one or more therapeutically equivalent alternative medications comprises identifying three or more therapeutically equivalent alternative medications, wherein at least two of the therapeutically equivalent alternative medications comprise a Payer preferred equivalent medication and at least one of the therapeutically equivalent alternative medications comprises a Prescriber's preferred equivalent medication.

15. The method of claim 11, further comprising providing the DSR to the Prescriber and the patient.

16. The method of claim 11, wherein the DSR shows the total savings for each of the therapeutically equivalent alternative medications corresponding to each of the patient's preexisting prescribed medications that has a lower cost than the corresponding preexisting prescribed medication.

17. The method of claim 11, wherein calculating the patient's savings and the total savings comprises calculating an annual patient's savings and an annual total savings.

18. The method of claim 11, wherein the rules specific to the Payer and Prescriber preferences include minimum threshold amounts to present the alternative medication for one or more of: patient cost savings and total savings.

19. The method of claim 11, wherein the triggering event further comprises is one or more of: the Prescriber requests evaluation of existing patient medications or the patient requests evaluation of existing medications.

20. The method of claim 11, wherein collecting the patient cost and total cost includes collecting a patient cost and total cost associated with each of the patient's one or more preexisting prescribed drugs and the one or more alternative drugs at an alternative pharmacy.

* * * * *